(12) United States Patent
Fowler et al.

(10) Patent No.: US 7,684,866 B2
(45) Date of Patent: Mar. 23, 2010

(54) APPARATUS AND METHODS FOR APPLYING NEURAL STIMULATION TO A PATIENT

(75) Inventors: Brad Fowler, Woodinville, WA (US); Bradford Evan Gliner, Sammamish, WA (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 0 days.

(21) Appl. No.: 10/910,775

(22) Filed: Aug. 2, 2004

(65) Prior Publication Data

US 2005/0070971 A1 Mar. 31, 2005

Related U.S. Application Data

(60) Provisional application No. 60/492,273, filed on Aug. 1, 2003.

(51) Int. Cl.
*A61N 1/00* (2006.01)
(52) U.S. Cl. .............................. 607/45; 607/2
(58) Field of Classification Search ............... 607/2, 607/40–59
See application file for complete search history.

(56) References Cited

U.S. PATENT DOCUMENTS

| | | | |
|---|---|---|---|
| 2,716,226 A | 8/1955 | Jonas | |
| 2,721,316 A | 10/1955 | Shaw | |
| 3,628,193 A | 12/1971 | Collins | |
| 3,650,276 A | 3/1972 | Burghele et al. | |
| 3,850,161 A | 11/1974 | Liss | |
| 4,019,518 A | 4/1977 | Maurer et al. | |
| 4,030,509 A | 6/1977 | Heilman et al. | |
| 4,125,116 A | 11/1978 | Fischell | |
| 4,140,133 A | 2/1979 | Kastrubin et al. | |
| 4,214,804 A | 7/1980 | Little | |

(Continued)

FOREIGN PATENT DOCUMENTS

DE 19750043 A1 5/1999

(Continued)

OTHER PUBLICATIONS

U.S. Appl. No. 60/325,872, filed Sep. 28, 2001, Sheffield.

(Continued)

*Primary Examiner*—Scott M Getzow
(74) *Attorney, Agent, or Firm*—Melissa Acosta; Peter Lando; Christopher S. L. Crawford

(57) ABSTRACT

Systems and methods for neural stimulation may include a stimulus unit; a first electrode assembly having a first set of contacts; and a second set of contacts. The stimulus unit can be an implantable pulse generator including a first terminal that can be biased at a first signal polarity and a second terminal that can be biased at a second signal polarity. The first electrode assembly includes a support member configured to be placed at the stimulation site, the first set of contacts carried by the support member, and a first lead configured to be attached to the first terminal of the implantable pulse generator for biasing the surface contacts at the first polarity. The second set of contacts is detached from the surface electrode assembly. The second set of contacts can be one or more conductive elements fixed to or forming portions of the implantable pulse generator, or a separate electrode array.

4 Claims, 12 Drawing Sheets

U.S. PATENT DOCUMENTS

| | | | |
|---|---|---|---|
| 4,245,645 A | 1/1981 | Picard et al. | |
| 4,308,868 A | 1/1982 | Jhabvala | |
| 4,328,813 A | 5/1982 | Ray | |
| 4,340,038 A | 7/1982 | McKean | |
| 4,390,023 A | 6/1983 | Rise | |
| 4,431,000 A | 2/1984 | Butler et al. | |
| 4,474,186 A | 10/1984 | Ledley et al. | |
| 4,532,931 A | 8/1985 | Mills | |
| 4,541,432 A | 9/1985 | Molina-Negro et al. | |
| 4,542,752 A | 9/1985 | DeHaan | |
| 4,590,946 A | 5/1986 | Loeb | |
| 4,607,639 A | 8/1986 | Tanagho | |
| 4,646,744 A | 3/1987 | Capel | |
| 4,817,634 A | 4/1989 | Holleman et al. | |
| 4,844,075 A | 7/1989 | Liss | |
| 4,865,048 A | 9/1989 | Eckerson | |
| 4,869,255 A | 9/1989 | Putz | |
| 4,903,702 A | 2/1990 | Putz | |
| 4,969,468 A | 11/1990 | Byers et al. | |
| 5,002,053 A | 3/1991 | Garcia-Rill | |
| 5,024,226 A | 6/1991 | Tan | |
| 5,031,618 A | 7/1991 | Mullett | |
| 5,044,368 A | 9/1991 | Putz | |
| 5,054,906 A | 10/1991 | Lyons | |
| 5,063,932 A | 11/1991 | Dahl et al. | |
| 5,092,835 A | 3/1992 | Schurig | |
| 5,119,832 A | 6/1992 | Xavier | |
| 5,121,754 A | 6/1992 | Mullett | |
| 5,143,089 A | 9/1992 | Alt | |
| 5,169,384 A | 12/1992 | Bosniak | |
| 5,184,620 A | 2/1993 | Cudahy et al. | |
| 5,193,540 A | 3/1993 | Schulman et al. | |
| 5,215,086 A | 6/1993 | Terry | |
| 5,215,088 A | 6/1993 | Normann et al. | |
| 5,224,491 A | 7/1993 | Mehra | |
| 5,255,678 A | 10/1993 | Deslauriers | |
| 5,263,967 A | 11/1993 | Lyons | |
| 5,269,303 A | 12/1993 | Wernicke et al. | |
| 5,271,417 A | 12/1993 | Swanson et al. | |
| 5,282,468 A | 2/1994 | Klepinski | |
| 5,299,569 A | 4/1994 | Wernicke et al. | |
| 5,303,705 A | 4/1994 | Nenov | |
| 5,304,206 A | 4/1994 | Baker | |
| 5,314,458 A | 5/1994 | Najafi et al. | |
| 5,342,410 A | 8/1994 | Braverman | |
| 5,358,513 A | 10/1994 | Powell | |
| 5,358,514 A | 10/1994 | Schulman et al. | |
| 5,370,672 A | 12/1994 | Fowler | |
| 5,405,375 A | 4/1995 | Ayers et al. | |
| 5,406,957 A | 4/1995 | Tansey | |
| 5,411,540 A | 5/1995 | Edell | |
| 5,417,719 A | 5/1995 | Hull | |
| 5,423,864 A | 6/1995 | Ljungstroem | |
| 5,423,877 A | 6/1995 | Mackey | |
| 5,441,528 A | 8/1995 | Chang et al. | |
| 5,458,631 A | 10/1995 | Xavier | |
| 5,464,446 A | 11/1995 | Dreessen et al. | |
| 5,470,846 A | 11/1995 | Sandyk | |
| 5,520,190 A | 5/1996 | Benedict et al. | |
| 5,522,864 A | 6/1996 | Wallace et al. | |
| 5,537,512 A | 7/1996 | Hsia | |
| 5,540,734 A | 7/1996 | Zabara | |
| 5,540,736 A | 7/1996 | Haimovich | |
| 5,549,655 A | 8/1996 | Erickson | |
| 5,562,708 A | 10/1996 | Combs et al. | |
| 5,575,813 A | 11/1996 | Edell | |
| 5,591,216 A | 1/1997 | Testerman | |
| 5,593,432 A | 1/1997 | Crowther, deceased et al. | |
| 5,601,611 A | 2/1997 | Fayram et al. | |
| 5,618,531 A | 4/1997 | Cherksey | |
| 5,628,317 A | 5/1997 | Starkebaum | |
| 5,674,251 A * | 10/1997 | Combs et al. | 607/4 |
| 5,674,264 A | 10/1997 | Carter et al. | |
| 5,676,655 A | 10/1997 | McCulloch et al. | |
| 5,683,422 A | 11/1997 | Rise | |
| 5,702,429 A | 12/1997 | King | |
| 5,707,334 A | 1/1998 | Young | |
| 5,711,316 A | 1/1998 | Elsberry | |
| 5,713,922 A | 2/1998 | King | |
| 5,713,923 A | 2/1998 | Ward | |
| 5,716,377 A | 2/1998 | Rise | |
| 5,722,401 A | 3/1998 | Pietroski | |
| 5,735,814 A | 4/1998 | Elsberry | |
| 5,750,376 A | 5/1998 | Weiss et al. | |
| 5,752,979 A | 5/1998 | Benabid | |
| 5,753,505 A | 5/1998 | Luskin | |
| 5,769,778 A | 6/1998 | Abrams et al. | |
| 5,772,591 A | 6/1998 | Cram | |
| 5,782,798 A | 7/1998 | Rise | |
| 5,782,873 A | 7/1998 | Collins | |
| 5,792,186 A | 8/1998 | Rise | |
| 5,797,970 A | 8/1998 | Pouvreau | |
| 5,814,014 A | 9/1998 | Elsberry | |
| 5,814,092 A | 9/1998 | King | |
| 5,824,021 A | 10/1998 | Rise | |
| 5,824,030 A | 10/1998 | Yang et al. | |
| 5,832,932 A | 11/1998 | Elsberry | |
| 5,833,603 A | 11/1998 | Kovacs et al. | |
| 5,833,709 A | 11/1998 | Rise | |
| 5,843,148 A | 12/1998 | Gijsbers | |
| 5,843,150 A | 12/1998 | Dressen | |
| 5,846,196 A | 12/1998 | Siekmeyer et al. | |
| 5,865,842 A | 2/1999 | Knuth et al. | |
| 5,871,517 A | 2/1999 | Abrams et al. | |
| 5,873,849 A | 2/1999 | Bernard | |
| 5,885,976 A | 3/1999 | Sandyk | |
| 5,886,769 A | 3/1999 | Zolten | |
| 5,893,883 A | 4/1999 | Torgerson | |
| 5,904,916 A | 5/1999 | Hirsch | |
| 5,913,882 A | 6/1999 | King | |
| 5,916,171 A | 6/1999 | Mayevsky | |
| 5,925,070 A | 7/1999 | King | |
| 5,928,144 A | 7/1999 | Real | |
| 5,938,688 A | 8/1999 | Schiff | |
| 5,938,689 A | 8/1999 | Fischell | |
| 5,941,906 A | 8/1999 | Barreras | |
| 5,964,794 A | 10/1999 | Bolz | |
| 5,975,085 A | 11/1999 | Rise | |
| 5,978,702 A | 11/1999 | Ward | |
| 5,983,140 A | 11/1999 | Smith | |
| 6,006,124 A | 12/1999 | Fischell | |
| 6,011,996 A | 1/2000 | Gielen | |
| 6,016,449 A | 1/2000 | Fischell | |
| 6,018,682 A | 1/2000 | Rise | |
| 6,021,352 A | 2/2000 | Christopherson | |
| 6,024,702 A | 2/2000 | Iversen | |
| 6,026,326 A | 2/2000 | Bardy | |
| 6,035,236 A | 3/2000 | Jarding et al. | |
| 6,038,480 A | 3/2000 | Hrdlicka et al. | |
| 6,042,579 A | 3/2000 | Elsberry | |
| 6,051,017 A | 4/2000 | Loeb et al. | |
| 6,052,624 A | 4/2000 | Mann | |
| 6,055,456 A | 4/2000 | Gerber | |
| 6,057,846 A | 5/2000 | Sever, Jr. | |
| 6,057,847 A | 5/2000 | Jenkins | |
| 6,058,331 A | 5/2000 | King | |
| 6,060,048 A | 5/2000 | Cherksey | |
| 6,061,593 A | 5/2000 | Fischell | |
| 6,066,163 A | 5/2000 | John | |
| 6,078,838 A | 6/2000 | Rubinstein | |
| 6,094,598 A | 7/2000 | Elsberry et al. | |
| 6,095,148 A | 8/2000 | Shastri et al. | |
| 6,104,956 A | 8/2000 | Naritoku | |
| 6,104,960 A | 8/2000 | Duysens | |

| | | | | | | |
|---|---|---|---|---|---|---|
| 6,111,911 | A | 8/2000 | Sanderford, Jr. et al. | 6,684,105 | B2 | 1/2004 | Cohen et al. |
| 6,122,548 | A | 9/2000 | Starkebaum | 6,687,525 | B2 | 2/2004 | Llinas |
| 6,126,657 | A | 10/2000 | Edwards | 6,690,974 | B2 | 2/2004 | Archer |
| 6,126,527 | A | 10/2000 | Howard, III et al. | 6,708,064 | B2 | 3/2004 | Rezai |
| 6,128,537 | A | 10/2000 | Rise | 6,725,094 | B2 | 4/2004 | Saberski |
| 6,128,538 | A | 10/2000 | Fischell | 6,735,475 | B1 | 5/2004 | Whitehurst et al. |
| 6,134,474 | A | 10/2000 | Fischell | 6,764,498 | B2 | 7/2004 | Mische |
| 6,152,143 | A | 11/2000 | Edwards | 6,782,292 | B2 | 8/2004 | Whitehurst |
| 6,161,044 | A | 12/2000 | Silverstone | 6,788,975 | B1 | 9/2004 | Whitehurst et al. |
| 6,161,045 | A | 12/2000 | Fischell | 6,795,737 | B2 | 9/2004 | Gielen et al. |
| 6,161,047 | A | 12/2000 | King et al. | 6,810,286 | B2 | 10/2004 | Donovan et al. |
| 6,176,242 | B1 | 1/2001 | Rise | 6,819,956 | B2 | 11/2004 | DiLorenzo |
| 6,190,893 | B1 | 2/2001 | Shastri et al. | 6,839,594 | B2 | 1/2005 | Cohen et al. |
| 6,198,958 | B1 | 3/2001 | Ives et al. | 6,850,802 | B2 | 2/2005 | Holsheimer |
| 6,205,360 | B1 | 3/2001 | Carter et al. | 6,871,098 | B2 | 3/2005 | Nuttin et al. |
| 6,205,361 | B1 | 3/2001 | Kuzma et al. | 6,873,872 | B2 | 3/2005 | Gluckman et al. |
| 6,210,417 | B1 | 4/2001 | Baudino et al. | 6,892,097 | B2 | 5/2005 | Holsheimer |
| 6,221,908 | B1 | 4/2001 | Kilgard et al. | 6,895,280 | B2 | 5/2005 | Meadows et al. |
| 6,230,049 | B1 | 5/2001 | Fischell et al. | 6,907,296 | B1 | 6/2005 | Doan et al. |
| 6,236,892 | B1 | 5/2001 | Feler | 6,922,590 | B1 | 7/2005 | Whitehurst |
| 6,246,912 | B1 | 6/2001 | Sluijter et al. | 6,934,580 | B1 | 8/2005 | Osorio et al. |
| 6,251,115 | B1 | 6/2001 | Williams et al. | 6,944,497 | B2 | 9/2005 | Stypulkowski |
| 6,263,225 | B1 | 7/2001 | Howard, III | 6,944,501 | B1 | 9/2005 | Pless |
| 6,263,237 | B1 | 7/2001 | Rise | 6,959,215 | B2 | 10/2005 | Gliner et al. |
| 6,280,462 | B1 * | 8/2001 | Hauser et al. ............... 607/5 | 6,990,377 | B2 | 1/2006 | Gliner et al. |
| 6,301,493 | B1 | 10/2001 | Marro et al. | 7,006,859 | B1 | 2/2006 | Osorio et al. |
| 6,304,787 | B1 | 10/2001 | Kuzma et al. | 7,010,351 | B2 | 3/2006 | Firlik et al. |
| 6,319,241 | B1 | 11/2001 | King et al. | 7,024,247 | B2 | 4/2006 | Gliner et al. |
| 6,339,725 | B1 | 1/2002 | Naritoku et al. | 7,050,856 | B2 | 5/2006 | Stypulkowski |
| 6,353,754 | B1 | 3/2002 | Fischell | 7,107,097 | B2 | 9/2006 | Stern et al. |
| 6,353,762 | B1 | 3/2002 | Baudino et al. | 7,110,820 | B2 | 9/2006 | Tcheng et al. |
| 6,354,299 | B1 | 3/2002 | Frischell | 7,112,319 | B2 | 9/2006 | Broderick et al. |
| 6,356,786 | B1 | 3/2002 | Rezai et al. | 7,146,222 | B2 | 12/2006 | Boling |
| 6,356,792 | B1 | 3/2002 | Errico et al. | 7,187,968 | B2 | 3/2007 | Wolf et al. |
| 6,360,122 | B1 | 3/2002 | Fischell | 7,187,977 | B2 | 3/2007 | Paul, Jr. |
| 6,366,813 | B1 | 4/2002 | DiLorenzo | 7,346,395 | B2 | 3/2008 | Lozano et al. |
| 6,375,666 | B1 | 4/2002 | Mische | 2001/0037134 | A1 | 11/2001 | Munshi |
| 6,381,496 | B1 | 4/2002 | Meadows et al. | 2001/0051819 | A1 | 12/2001 | Fischell et al. |
| 6,393,319 | B1 | 5/2002 | Bock et al. | 2001/0053885 | A1 | 12/2001 | Gielen et al. |
| 6,405,079 | B1 | 6/2002 | Ansarinia | 2002/0028072 | A1 | 3/2002 | Kashiyama |
| 6,418,344 | B1 | 7/2002 | Rezai | 2002/0062143 | A1 | 5/2002 | Baudino et al. |
| 6,421,566 | B1 | 7/2002 | Holsheimer et al. | 2002/0077670 | A1 * | 6/2002 | Archer et al. ............. 607/45 |
| 6,425,852 | B1 | 7/2002 | Epstein et al. | 2002/0087201 | A1 * | 7/2002 | Firlik et al. ............. 607/45 |
| 6,427,086 | B1 | 7/2002 | Fischell | 2002/0091419 | A1 * | 7/2002 | Firlik et al. ............. 607/45 |
| 6,456,886 | B1 | 9/2002 | Howard, III et al. | 2002/0099295 | A1 | 7/2002 | Gil et al. |
| 6,459,936 | B2 | 10/2002 | Fischell | 2002/0099412 | A1 | 7/2002 | Fischell |
| 6,463,328 | B1 | 10/2002 | John | 2002/0169485 | A1 | 11/2002 | Pless |
| 6,464,356 | B1 | 10/2002 | Sabel | 2003/0028072 | A1 | 2/2003 | Fischell et al. |
| 6,466,822 | B1 | 10/2002 | Pless | 2003/0074032 | A1 | 4/2003 | Gliner |
| 6,473,568 | B2 | 10/2002 | Kashiyama | 2003/0078633 | A1 | 4/2003 | Firlik et al. |
| 6,473,639 | B1 | 10/2002 | Fischell | 2003/0088274 | A1 | 5/2003 | Gliner et al. |
| 6,480,743 | B1 | 11/2002 | Kirkpatrick | 2003/0097159 | A1 | 5/2003 | Schiff et al. |
| 6,484,059 | B2 | 11/2002 | Gielen | 2003/0097161 | A1 | 5/2003 | Firlik et al. |
| 6,487,450 | B1 | 11/2002 | Chen | 2003/0114886 | A1 | 6/2003 | Gluckman et al. |
| 6,497,699 | B1 | 12/2002 | Ludvig et al. | 2003/0125772 | A1 * | 7/2003 | Olson et al. ............. 607/5 |
| 6,499,488 | B1 | 12/2002 | Hunter et al. | 2003/0125786 | A1 | 7/2003 | Gliner et al. |
| 6,505,075 | B1 | 1/2003 | Weiner | 2003/0130706 | A1 | 7/2003 | Sheffield et al. |
| 6,507,755 | B1 | 1/2003 | Gozani et al. | 2003/0149457 | A1 | 8/2003 | Tcheng et al. |
| 6,529,774 | B1 | 3/2003 | Greene | 2003/0176901 | A1 | 9/2003 | May |
| 6,539,263 | B1 | 3/2003 | Schiff et al. | 2003/0181954 | A1 | 9/2003 | Rezai |
| 6,549,814 | B1 | 4/2003 | Strutz et al. | 2003/0187490 | A1 | 10/2003 | Gliner |
| 6,556,868 | B2 | 4/2003 | Naritoku et al. | 2003/0187491 | A1 | 10/2003 | Greenberg et al. |
| 6,569,654 | B2 | 5/2003 | Shastri et al. | 2003/0195602 | A1 | 10/2003 | Boling |
| 6,591,138 | B1 | 7/2003 | Fischell et al. | 2003/0233137 | A1 | 12/2003 | Paul |
| 6,597,954 | B1 | 7/2003 | Pless et al. | 2004/0073270 | A1 | 4/2004 | Firlik et al. |
| 6,609,030 | B1 | 8/2003 | Rezai et al. | 2004/0082847 | A1 | 4/2004 | McDermott |
| 6,609,031 | B1 | 8/2003 | Law et al. | 2004/0088024 | A1 | 5/2004 | Firlik et al. |
| 6,615,065 | B1 | 9/2003 | Barrett et al. | 2004/0092809 | A1 | 5/2004 | DeCharms |
| 6,622,048 | B1 | 9/2003 | Mann | 2004/0102828 | A1 | 5/2004 | Lowry et al. |
| 6,631,295 | B2 | 10/2003 | Rubinstein et al. | 2004/0111127 | A1 | 6/2004 | Gliner et al. |
| 6,633,780 | B1 | 10/2003 | Berger | 2004/0138550 | A1 | 7/2004 | Hartlep et al. |
| 6,647,296 | B2 | 11/2003 | Fischell et al. | 2004/0158298 | A1 * | 8/2004 | Gliner et al. ............. 607/48 |
| 6,665,562 | B2 | 12/2003 | Gluckman et al. | 2004/0176831 | A1 | 9/2004 | Gliner et al. |

| | | |
|---|---|---|
| 2004/0181263 A1 | 9/2004 | Balzer et al. |
| 2004/0215287 A1 | 10/2004 | Swoyer et al. |
| 2004/0215288 A1 | 10/2004 | Lee et al. |
| 2004/0236388 A1 | 11/2004 | Gielen et al. |
| 2004/0243205 A1 | 12/2004 | Keravel et al. |
| 2004/0249422 A1 | 12/2004 | Gliner et al. |
| 2005/0004620 A1* | 1/2005 | Singhal et al. ............. 607/45 |
| 2005/0015129 A1 | 1/2005 | Mische |
| 2005/0021104 A1 | 1/2005 | DiLorenzo |
| 2005/0021105 A1 | 1/2005 | Firlik et al. |
| 2005/0021106 A1 | 1/2005 | Firlik et al. |
| 2005/0021107 A1 | 1/2005 | Firlik et al. |
| 2005/0021118 A1 | 1/2005 | Genau et al. |
| 2005/0033378 A1 | 2/2005 | Sheffield et al. |
| 2005/0033379 A1 | 2/2005 | Lozano et al. |
| 2005/0070971 A1 | 3/2005 | Fowler et al. |
| 2005/0075679 A1 | 4/2005 | Gliner et al. |
| 2005/0075680 A1 | 4/2005 | Lowry et al. |
| 2005/0090756 A1 | 4/2005 | Wolf et al. |
| 2005/0096701 A1 | 5/2005 | Donovan et al. |
| 2005/0113882 A1 | 5/2005 | Cameron et al. |
| 2005/0119712 A1 | 6/2005 | Shafer |
| 2005/0154425 A1 | 7/2005 | Boveja et al. |
| 2005/0154426 A1 | 7/2005 | Boveja et al. |
| 2005/0182453 A1 | 8/2005 | Whitehurst |
| 2005/0228451 A1 | 10/2005 | Jaax et al. |
| 2006/0004422 A1 | 1/2006 | De Ridder |
| 2006/0004423 A1 | 1/2006 | Boveja et al. |
| 2006/0015153 A1 | 1/2006 | Gliner et al. |
| 2006/0020297 A1 | 1/2006 | Gerber et al. |
| 2006/0064138 A1 | 3/2006 | Velasco et al. |
| 2006/0095088 A1 | 5/2006 | De Ridder |
| 2006/0106430 A1 | 5/2006 | Fowler et al. |
| 2006/0106431 A1 | 5/2006 | Wyler et al. |
| 2006/0129205 A1* | 6/2006 | Boveja et al. ............. 607/45 |
| 2006/0173522 A1 | 8/2006 | Osorio |
| 2006/0217782 A1 | 9/2006 | Boveja et al. |
| 2006/0241717 A1 | 10/2006 | Whitehurst et al. |
| 2006/0259094 A1 | 11/2006 | Naisberg et al. |
| 2007/0032834 A1 | 2/2007 | Gliner et al. |
| 2007/0032839 A1 | 2/2007 | Parramon et al. |
| 2007/0060974 A1 | 3/2007 | Lozano |
| 2007/0078495 A1 | 4/2007 | Caillat et al. |

FOREIGN PATENT DOCUMENTS

| | | |
|---|---|---|
| EP | 0214527 | 3/1987 |
| EP | 0319844 A1 | 6/1989 |
| EP | 1180056 | 9/2000 |
| EP | 0 998 958 A2 | 10/2000 |
| EP | 1 145 736 | 10/2001 |
| WO | WO87/07511 | 12/1987 |
| WO | WO94/07564 | 4/1994 |
| WO | WO95/21591 | 8/1995 |
| WO | WO 97-45160 | 12/1997 |
| WO | WO98/06342 | 2/1998 |
| WO | WO-0007494 | 2/2000 |
| WO | WO-0040295 | 7/2000 |
| WO | WO 01/97906 | 12/2001 |
| WO | WO-0193953 | 12/2001 |
| WO | WO 02/09811 | 2/2002 |
| WO | WO 02/36003 | 5/2002 |
| WO | WO 02/38031 | 5/2002 |
| WO | WO 02/38217 | 5/2002 |
| WO | WO-02073526 | 9/2002 |
| WO | WO 03/082402 | 3/2003 |
| WO | WO 03/043690 | 5/2003 |
| WO | WO 03-101532 | 12/2003 |

OTHER PUBLICATIONS

U.S. Appl. No. 60/325,978, filed Sep. 28, 2001, Gliner.
Bel, S. and Bauer, B.L., "Dorsal Column Stimulation (DCS): Cost to Benefit Analysis," Acta Neurochirurgica, Suppl. 52, pp. 121-123 (1991).
Benabid, A. L. et al, "Chronic electrical stimulation of the ventralis intermedius nucleus of the thalamus as a treatment of movement disorders," J. Neurosurg., Apr. 1997, 86(4); 737; http://www.ncbi.nlm.nih.gov; [accessed Nov. 18, 2003].
Butefisch et al., "Mechanisms of use-dependent plasticity in the human motor cortex," Proc. Natl. Acad. Sci. USA, vol. 97, No. 7, pp. 3661-3665 (Mar. 2000).
Canavero, S. and Paolotti, R., "Extradural Motor Cortex Stimulation afor Advanced Parkinson's Disease: Case Report," Movement Disorders, 15(1):169-171,2000.
Cincotta et al., "Reorganization of the motor cortex in a patient with congenital hemiparesis and mirror movements," Neurology, vol. 55, pp. 129-131 (2000).
Classen, et al., "Rapid Plasticity of Human Cortical Movement Representation Induced by Practice," The Journal of Neurophysiology, vol. 79, No. 2, pp. 1117-1123 (Feb. 1998).
Cohen et al., "Studies of Neuroplasticity With Transcranial Magnetic Stimulation," The Journal of Clinical Neurophysiology, vol. 15, No. 4 (1998).
Cramer, S.C. and Bastings, E.P., "Mapping clinically relevant plasticity after stroke," Neuropharmacology vol. 19, No. 5, pp. 842-851 (Apr. 2000).
Dam et al., "Effects of Fluoxetine and Maprotiline on Functional Recovery in Poststroke Hemiplegic Patients Undergoing Rehabilitation Therapy," Stroke, vol. 27, No. 7, pp. 1211-1214 (Jul. 1996).
Feys et al., "Value of somatosensory and motor evoked potentials in predicting arm recovery after a stroke," (Oct. 1999).
Franzini et al., "Reversal of thalamic hand syndrome by long-term motor cortex stimulation," Journal of Neurosurgery 93:873-875 (2000).
Gladstone et al., "Enhancing Recovery after Stroke with Noradrenergic Pharmacotherapy: A New Frontier?,"Can J. Neurol. Sci., vol. 27, No. 2 (May 2000).
Gordon et al., "Parameters for direct cortical electrical stimulation in the human: histopathologic confirmation," Electroencephalography and clinical Neurophysiology, vol. 75, pp. 371-377 (1990).
Hodge, Jr., C.J. and Boakye, M., "Biological Plasticity: The Future of Science in Neurosurgery," Neurosurgery, vol. 48, No. 1 (Jan. 2001).
Kauhanen et al., "Domans and Determinants of Quality of Life After Stroke Caused by Brian Infarction," Arch. Phys. Med. Rehabil., vol. 81, pp. 1541-1546 (Dec. 2000).
Kopell et al., "The Continuing Evolution of Psychiatric Neurosurgery," CNS Spectrums, vol. 5, No. 10, pp. 20-31 (Oct. 2000).
Levy et al., "Functional MRI Evidence of Cortical Reorganization in Upper-Limb Stroke Hemiplegia Treated with Constraint-Induced Movement Therapy," American Journal of Physical Medicine & Rehabilitation, vol. 80, No. 1, pp. 4-7 (2001).
Liepert et al., "Treatment-Induced Cortical Reorganization After Stroke in Humans," Stroke, 31:1210-1216 (2000).
Malenka, R.C. and Nicoll, R.A., "Long-Term Potenetiation—A Decade of Progress?," Neuroscience, vol. 285, No. 5435, Issue of Sep. 17, 1999, pp. 1870-1874.
Martinez et al., "Motor hand recovery after stroke Prognostic yield of early transcranial magnetic stimulation," Electromyography. Clin. Neurophysiology, vol. 39, pp. 405-410 (1999).
Netz et al., "Reorganization of motor output in the non-affected hemisphere after stroke," Brain, 120, 99. 1579-1586 (1997).
Nitsche, M.A. and Paulus, W., "Excitability changes induced in the human motor cortex by weak transcranial direct current stimulation," The Journal of Physiology, vol. 527.3, pp. 663-639 (2000).
Oliveri et al., "Paired transcranial magnetic stimulation protocols reveal a pattern of inhibition and facilitation in the human parietal cortex," The Journal of Physiology, 529.2, pp. 461-468 (2000).
Pascual-Leone et al., "Study and Modulation of Human Cortical Excitability With Transcranial Magnetic Stimulation," Journal of Clinical Neurophysiology, vol. 15, No. 4 (1998).
Pascual-Leone et al., "Transcranial magnetic stimulation and neuroplasticity," Neurophycologia 37, pp. 207-217 (1999).

Rezai, "Neurostimulation," Neurological Research, vol. 22, No. 3 pp. 235-273 (Apr. 2000).
Rossi et al., "Effects of Repetitive Transcranial Magnetic Stimulation on Movement-related Cortical Activity in Humans," Cerebral Cortex, vol. 10, No. 8, pp. 802-808 (Aug. 2000).
Roux et al., "Chronic Motor Cortex Stimulation for Phantom Limb Pain: A Functional Magnetic Resonance Imagining Study: Technical Cast Report," Neurosurgery, vol. 49, No. 3 (Mar. 2001).
Saitou et al., "Cerebral Blood Volume and Oxygenation Among Poststroke Hemiplegic Patients: Effects of 13 Rehabilitation Tasks Measured by Near-Infrared Spectroscopy," Arch. Phys. Med. Rehabil., vol. 81 pp. 1348-1356 (Oct. 2000).
Sandkuhler, "Learning and memory in pain pathways," Pain 88, pp. 113-118 (2000).
Sanes, "The Relation between Human Brain Activity and Hand Movements," NeuroImage 11, pp. 370-374 (2000).
Sanes, J. and Donoghue, J.P., "Plasticity and Primary Motor Cortex," Annual Review of Neuroscience 23:393-415 (2000).
Schiff et al., "A neuromodulation strategy for rational therapy of complex brain injury states," Neurological Research, vol. 22 pp. 267-272 (Apr. 2000).
Shimizu et al., "Therapeutic efficacy of transcranial magnetic stimulation for hereditary spinocerebellar degeneration," Tohoku Journal of Experimental Medicine, 189(3):203-11 (Nov. 1999).
Siebner et al., "Lasting cortical activation after repetitive TMS of the motor cortex," NEUROLOGY 54, pp. 956-963 (Feb. 2000).
Stefan et al., "Induction of plasticity in the human motor cortex by paired associative stimulation," Brain, 123, pp. 572-584 (2000).
Turton et al., "Contralateral and ipsilateral EMG responses to transcranial magnetic stimulation during recovery of arm and hand function after stroke," Electroencephalography and Clinical Neurophysiology 101 pp. 316-328 (1996).
Turton, A. and Lemon, R.N., "The contribution of fast corticospinal input to the voluntary activation of proximal muscles in normal subjects and in stroke patients," Exp. Brain Res., vol. 129, pp. 559-572 (1999).
Van Der Lee et al., "The Intra- and Interrater Reliability of the Action Research Arm Test: A Practical Test of Upper Extremity Function in Patients With Stroke," Arch. Phys. Med. Rehabil., vol. 82 pp. 14-19 (Jan. 2001).
Walker-Batson et al., "Amphetamine Paired With Physical Therapy Accelerates Motor Recovery After Stroke," Stroke, vol. 26, No. 12, pp. 2254-2259 (1995).
Ziemann et al., "Modulation of Plasticity in Human Motor Cortex after Forearm Ischemic Nerve Block," The Journal of Neuroscience, vol. 18, No. 3, pp. 1115-1123 (Feb. 1998).
Behrens, T. et al., "Non-invasive mapping of connections between human thalamus and cortex using diffusion imaging," Nature Neuroscience, vol. 6, No. 7, pp. 750-757 (Jul. 2003).
Di Lazzaro, V. et al., "Theta-burst repetitive transcranial magnetic stimulation suppressess specific excitatory circuits in the human motor cortex," Physiology in Press: published online on Apr. 21, 2005 as 10.1113/jphysio.2005.087288.
Hummel, Friedhelm et al., "Effects of non-invasive cortical stimulation on skilled motor function in chronic stroke," Brain Advance Access, Jan. 5, 2005, pp. 1-10, Brain.
Kilgard, Michael et al., "Cortical Map Reorganization Enabled by Nucleus Basalis Activity," Science, vol. 279 pp. 1714-1717 (Mar. 13, 1998).
Lang, Nicolas et al., "Preconditioning with Transcranial Direct Current Stimulation Sensitizes the Motor Cortex to Rapid-Rate Transcranial Magnetic Stimulation and Controls the Direction of After-Effects," Biol Psychiatry 2004:56:634-639, 2004 Society of Biological Psychiatry.
Lazar, M. et al., "White Matter Tractography Using Diffusion Tensor Deflection," Human Brain Mapping, 18:306-321, (2003).
Nitsche, Michael A. et al., "Level of action of cathodal DC polarisation induced inhibition of the human motor cortex," Dec. 2, 2002, Clinical Neurophysiology 114 (2003) 600-604.
Nitsche, Michael A., et al. "Facilitation of Implicit Motor Learning by Weak Transcranial Direct Current Stimulation of the Primary Motor Cortex in the Human," Journal of Cognitive Neuroscience 15:4, pp. 619-626, 2003 Massachusetts Institute of Technology.

Paulus, W, "Supplements to Clinical Neurophysiology," Transcranial Magnetic Stimulation and Transcranial Direct Current Stimulation (Supplements to Clinical Neurophysiology; vol. 56), pp. 249-254, 2003 Elsevier Science, B.V.
Strens, Lucy et al., "The ipsilateral Human Motor Cortex Can Functionally Compensate for Acute Contralateral Motor Cortex Dysfunction," Current Biology, vol. 13, pp 1201-1205 (Jul. 15, 2003).
Tsubokawa, T., "Chronic Motor Cortex Stimulation in Patients with Thalamic Pain," J. Neurosurg 78:393-401, (Mar. 1993).
Tuch, D. et al., "Conductivity Tensor Mapping of the Human Brain Using Diffusion Tensor MRI," Neurobiology, vol. 98 No. 20, pp. 11697-11701 (Sep. 25, 2001).
Theoret, Hugo et al., "Exploring Paradoxical Functional Facilliation with TMS," Supplements to Clinical Neurophysiology, vol. 56, pp. 211-219 (2003).
Tsubokawa, T. et al., "Chronic Motor Cortex Stimulation for the Treatment of Central Pain", Acta Neurochirurgica, Suppl. 52, pp. 137-139 (1991).
International Search Report and Written Opinion for International Application No. PCT/US04/25010, mailed Aug. 4, 2005, 9 pages.
Barr, Deborah et al., "Induction and Reversal of Long-Term Potentiation by Low-and High- Intensity Theta Pattern Stimulation," The Journal of Neuroscience, 15(7): pp. 5402-5410 (Jul. 1995).
Brain Electrical Stimulation to Enhance Recovery After Stroke. ClinicalTrials.gov.[Retrieved on Dec. 22, 2005]. Retrieved from the internet <URL http://www.clinicaltrials.gov/ct/show/NCT00085657?order=2>.
Burnett, Mark G. et al., "Diffuse optical measurement of blood flow, blood oxygenation, and metabolism in a human brain during sensorimotor cortex activation," Optics Letters, vol. 29, No. 15, pp. 1766-1768 (Aug. 1, 2004).
Cytokines Web Clinical Significance. Cytokines Web, 2 pages. [Retrieved on Sep. 2, 2005]. Retrieved from the internet: <URL: http://cmbi.bjmu.edu.cn/cmbidata/cgf/CGF_Database/cytweb/roles/index.html>.
Ding, Yuemin et al., "Neural Plasticity After Spinal Cord Injury," Current Pharmaceutical Design vol. 11, No. 11, pp. 1441-1450, Abstract Only- 1 page (Apr. 2005).
De Ridder, Dirk et al., "Magnetic and electrical stimulation of the auditory cortex for intractable tinnitus," Journal Neurosurg., vol. 100, pp. 560-564, (Mar. 2004).
Duncan, Pamela W. et al., "Defining post-stroke recovery: implications for design and interpretation of drug trials," Neuropharmacology vol. 39, pp. 835-841 (2000).
Fregni, Felipe et al., "Anodal Transcranial Direct Current Stimulation of Prefrontal Cortex Enhances Working Memory," Experimental Brain Research vol. 166, No. 1, pp. 23-30 (Sep. 2005).
Hagemann, Georg et al., "Increased Long-Term Potentiation in the Surround of Experimentally Induced Focal Cortical Infarction," Annals of Neurology, vol. 44, No. 2, pp. 255-258 (Aug. 1998).
Hayakawa, Toshiji et al., "Changes in Cerebral Oxygenation and Hemodynamics During Obstructive Sleep Apneas," Chest, vol. 109, pp. 916-921 (1996).
Hoshi, Yoko et al., "Detection of dynamic changes in cerebral oxygenation coupled to neuronal function during mental work in a man," Neuroscience Letters, vol. 150, pp. 5-8 (1993).
Hoshino et al., "Application of multichannel near-infrared spectroscopic topography to physiological monitoring of the cortex during cortical mapping: technical case report," Surgical Neurology, vol. 64, pp. 272-275 (2005).
Huang, Ying-Zu et al., "Theta Burst Stimulation of the Human Motor Cortex," Neuron, vol. 45, pp. 201-206 (Jan. 20, 2005).
Larson, John et al., "Reversal of LTP by theta frequency stimulation," Brain Research, 600: pp. 97-102 (1993).
L-DOPA dyskinesias. BioChemistry of PD. [Retrieved on Dec. 22, 2005]. Retrieved from the internet <URL http://www.mayo.edu/fdp/pd-info/dyskinesias.htm>.
Mansur, C.G., et al., "A sham stimulation-controlled trial of rTMS of the unaffected hemisphere in stroke patients," Neurology, vol. 64, pp. 1802-1804 (2005).
Martin et al.; "Transcranial Magnetic Stimulation as a Complementary Treatment for Aphasia," Semin Speech Language vol. 25, pp: 181-191 (2004) Abstract only- 1 page.

Panchanathan, Sethuraman et al., "Rehabilitation of patients with hemispatial neglect using visual-haptic feedback in Virtual reality environment," [Retrieved on Dec. 22, 2005]. Retrieved from the internet <URL http://www.public.asu.edu/~tmcdani/publication.htm>.

Paulus, Walter, "Toward Establishing a Therapeutic Window for rTMS by Theta Burst Stimulation," Neuron, vol. 45, pp. 181-183 (Jan. 20, 2005).

Penn, Michael, "Stemming Parkinson's" On Wisconsin Allumni Magazine, Summer 2003, [Retrieved on Dec. 22, 2005]. Retrieved from the internet <URL http://www.uwalumni.com/onwisconsin/2003_summer/research.html>.

Schaefer, Pamela W. et al., "Assessing Tissue Viability with MR Diffusion and Perfusion Imaging," AJNR, 24: pp. 436-443 (Mar. 2003).

Schiene, Klaus et al., "Neuronal Hyperexcitability and Reduction of GABA-Receptor Expression in the Surround of Cerebral Photothrombosis," Journal of Cerebral Blood Flow and Metabolism, vol. 16, No. 5, pp. 906-914 (1996).

SCIRun. Scientific Computing and Imaging Institute, 2 pages. [Retrieved on Jul. 24, 2005]. Retrieved from the internet: <URL: http://sofware.sci.utah.edu/scirun.html>.

Strangman, Gary et al., "Non-Invasive Neuroimaging Using Near-Infrared Light," Biological Psychiatry, vol. 52, pp. 679-693 (2002).

Strangman, Gary et al., "A Quantitative Comparison of Simultaneous BOLD fMRI and NIRS Recordings during functional Brain Activation," NeuroImage, vol. 17, pp. 719-731 (2002).

Strangman, Gary et al., "Factors affecting the accuracy of near-infrared spectroscopy concentration calculations for focal changes in oxygenation parameters," NeuroImage, vol. 18, pp. 865-879 (2003).

The INVOS Cerebral Oximeter. Somanetics, 1 page (Retrieved on Dec. 22, 2005). Retrieved from the internet: <URL http://www.somanetics.net/invos.htm>.

The GES 250 for Dense-Array EEG Research. Electrical Geodesics, Inc., 3 pages. [Retrieved on Aug. 25, 2005]. Retrieved from the internet: <URL: http://www.egi.com/ges250r_n.html>.

TAGA, Gentaro et al., "Brain Imaging in awake infants by near-infrared optical topography," PNAS, vol. 100, No. 19, pp. 10722-10727 (Sep. 16, 2003).

Thomas, Carmen et al., "Do Children with aggressive behavior have temporal lobe changes?" Alasbimn Journal, Year 5, No. 19, 8 pages (Jan. 2003).

Toronov, Vlad et al., "Near-infrared study of fluctuations in cerebral hemodynamics during rest and motor stimulation: Temporal analysis and spatial mapping," Medical Physics, vol. 27, No. 4, pp. 801-815 (Apr. 2000).

Tractography. Absolute Astronomy Reference, 2 pages. [Retrieved on Jul. 24, 2005]. Retrieved from the internet: <URL: http://www.absoluteastronomy.com/encyclopedia/T/Tr/Tractography.htm>.

Weinand, Martin E. et al., "Cerebral blood flow and temporal lobe epileptogenicity," [Retrieved on Dec. 22, 2005]. Retrieved from the internet: <URL http://www.aans.org/education/journal/neurosurgical/nov96/1-5-3.asp>.

Meyerson, B.A. et al., "Motor Cortex Stimulation as Treatment of Trigeminal Neuropathic Pain", Acta Neurochirurgica Supplementum, vol. 58, pp. 150-153 (1993).

Tsubokawa, T. et al., "Treatment of Thalamic Pain by Chronic Motor Cortex Stimulation", PACE, vol. 14, pp. 131-134 (Jan. 1991).

Bury, Scott et al., "The Effects of Behavioral Demand on Motor Cortical and Cerebellar Structural Plasticity After Brain Injury in Adult Rats," (Retrieved on Mar. 1, 2003). Retrieved from the internet: <URL:http://www.mcmaster.ca/inabis98/schallert/bury0827/two.html#introduction>.

Keyvani, Kathy et al., "Suppression of proteasome C2 contralateral to ischemic lesions in rat brain," Brain Research, vol. 858, pp. 386-392, 2000.

Nudo, Randolph J., et al., "Recovery after damage to motor cortical areas," Current Opinion in Neurobiology, vol. 9, Issue 6, pp. 740-747, Dec. 1, 1999.

Cao, Yue et al., "Cortical Language Activation in Stroke Patients Recovering From Aphasia With Functional MRI," Stroke, vol. 30, pp. 2331-2340, Nov. 1999.

Bluestone, Avraham Y. et al., "Three-dimensional optical tomography of hemodynamics in the human head," Optics Express, vol. 9, No. 6, pp. 272-286 (Sep. 10, 2001).

How Imagent™ Works. ISS Inc., 1 page [Retrieved on Oct. 14, 2005]. Retrieved from the internet: <URL http://www.iss.com/Products/imagent_fmri.html>.

Imagent™ Functional Brain Imaging System. ISS, Inc., 2 pages [Retrieved on Oct. 14, 2005]. Retrieved from the internet: <URL http://www.iss.com/Products/imagent.html>.

Imagent™ functional Near Infrared Imaging System (fNIRS) Brain Imaging Using Infrared Photons. ISS Inc., 8 pages [Retrieved on Oct. 14, 2005]. Retrieved from the internet: <URL http://www.iss.com/products/imagent/Imagent™.pdf>.

Janicek, Milos J. et al., "Dynamic Infrared Imaging of Newly Diagnosed Malignant Lymphoma Compared with Gallium-67 and Fluorine-18 Fluorodeoxyglucose (FDG) Positron Emission Tomography," Technology in Cancer Research and Treatment, vol. 2, No. 6, pp. 571-577 (Dec. 2003).

Tang, Cha-Min et al., "Optical Coherence Tomography of the Human Basal Ganglion," Deep Brain Stimulation Consortium Meeting Program Book, Sep. 29-30, 2003, Washington DC.

Timmermann, Lars et al., "The cerebral oscillatory network of parkinsonian resting tremor," Brain, vol. 26, pp. 199-212, (2003).

Yokoh, Arika et al., "Intermittent versus continuous brain retraction," Journal of Neurosurgery, vol. 58, pp. 918-923 (Jun. 1983).

Montgomery, "Thalamic Stimulation," Neurosdence Pathways, The Cleveland Clinic Foundation, 2 pages.

Schulz et al., "Localization of Epileptic Auras Induced on Stimulation by Subdural Electrodes," Epilepsia, Dec. 1997, vol. 38, Issue 12, pp. 1321-1329.

Storer et al., "Microiontophoretic application of serotonin (5HT)1B/1D agonists Inhibits trigeminal cell firing in the cat," Brain, 1997, vol. 120, Issue 12, pp. 2171-2177, Oxford University Press.

Suzuki et al., "Selective Electrical Stimulation of Postganglionic Cerebrovascular Parasympathetic Nerve Fibers Originating from the Sphenopalatine Ganglion Enhances Cortical Blood Flow in the Rat," Journal of Cerebral Blood Flow and Metabolism, May 1990, 10(3):383-91.

Vanderkooy et al., "Resolution Below the Least Significant Bit in Digital Systems with Dither," JAES, Mar. 1984, vol. 32, No. 3, pp. 106-113.

U.S. Appl. No. 10/583,630, filed Jun. 20, 2006, Lozano.
U.S. Appl. No. 11/254,060, filed Oct. 19, 2005, Wyler.
U.S. Appl. No. 11/254,240, filed Oct. 19, 2005, Wyler.
U.S. Appl. No. 11/255,187, filed Oct. 19, 2006, Firlik.
U.S. Appl. No. 11/344,453, filed Jan. 30, 2006, Gliner.
U.S. Appl. No. 11/518,139, filed Sep. 7, 2006, Weinand.
U.S. Appl. No. 11/583,349, filed Oct. 18, 2006, Sloan.
U.S. Appl. No. 11/638,326, filed Dec 12, 2006, Gliner et al.

CNN.com, Health, "Lab Zaps Strokes with Magnetic Pulses," http://www.cnn.com/2004/HEALTH/conditions/11/29/zapping.strokes.ap/, Nov. 29, 2004, 4 pages [Retrieved on Dec. 2, 2004].

Beveridge, J. A., "Use of Exogenous Electric Current in the Treatment of Delayed Lesions in Peripheral Nerves," Plastic and Reconstructive Surgery, Oct. 1988, vol. 82, No. 4, pp. 573-579.

Mendonca, A.C., "Directly applied low intensity direct electric current enhances peripheral nerve regeneration in rats," Journal of Neuroscience Methods, 2003, vol. 129, pp. 183-190.

Politis, M. J., "Mammalian Optic Nerve Regeneration Following the Application of Electric Fields," The Journal of Trauma, Nov. 1988, vol. 28, No. 11, pp. 1548-1552.

Binder, J. M.D., "Functional Magnetic Resonance Imaging: Language Mapping," Neurosurgery Clinics of North America, vol. 8, No. 3, Jul. 1997, pp. 383-392.

Kelly-Spratt, K. "Transfection of PC-12 cells: a model system for primary neuronal cells," Qiagen News, Customer application article, www.qiagen.com, Issue 4, 1998, 2 pages.

Kimura, K. et al., "Electrically induced neurite outgrowth of PC12 cells on the electrode surface," Entrez PubMed, http://www.ncbi.nlm.nlh.gov/entrez/query.fcgi?db=pubmed&cmd=Retrieve&dopt=Abstract, 1 page.

Ferrari, A. et al., "Immature human NT2 cells grafted into mouse brain differentiate into neuronal and glial cell types," FEBS Letters, Dec. 8, 2000, pp. 121-125, vol. 486, No. 2, Elsevier Science B.V., Amsterdam.

Price, J. et al., "Neurotransplantation in neurodegenerative disease: a survey of relevant issues in developmental neurobiology," Novartis Foundation Symposium 231, 2000, pp. 148-165, Wiley, Chichester, UK.

Woodbury, D. et al., "Adult Rat and Human Bone Marrow Stromal Cells Differentiate Into Neurons," Journal of Neuroscience Research, 2000, vol. 61, pp. 364-370, Wiley Interscience, New York, NY.

Bezard et al., "Cortical Stimulation and Epileptic Seizure: A Study of the Potential Risk in Primates," Neurosurgery, vol. 45, No. 2, Aug. 1999, 346-350.

Cramer et al., "Use of Functional MRI to Guide Decisions in a clinical Stroke Trial," Stroke, Journal of the American Heart Association, May 2005, pp. e50-e52, American Heart Association, Dallas TX.

Cicinelli et al., "Transcranial magnetic stimulation reveals an interhemispheric asymmetry of cortical inhibition in focal epilepsy," Neurophysiology, vol. 11, No. 4 Mar. 20, 2000, pp. 701-707.

Cincotta et al., "Suprathreshold 0.3 Hz repetitive TMS prolongs the cortical silent period: Potential Implications for therapeutic trials in epilepsy," Clinical Neurophysiology, vol. 114, 2003, pp. 1827-1833, Elsevier Ireland Ltd.

Fregni et al., "Antiepileptic Effects of Repetitive Transcranial Magnetic Stimulation in Patients with Cortical.Malformations: An EEG and Clinical Study," ASSFN Proceedings 2004, Stereotactic and Functional Neurosurgery, 2005, 83:57-62.

Haglund, Michael M. et al., "Optical imaging of epileptiform and functional activity in human cerebral cortex," Nature, Aug. 20, 1992, pp. 668-671, vol. 358, Nature Publishing Group.

Kinoshita et al., "Electric cortical stimulation suppresses epileptic and background activities in neocortical epilepsy and mesial temporal lobe epilepsy," Clinical Neurophysiology, vol. 116, 2005, pp. 1291-1299, Elsevier Ireland Ltd.

Kossoff et al., "Effect of an External Responsive Neurostimulator on Seizures and Electrographic Discharges during Subdural Electrode Monitoring," Epilepsia 45(12):1560-1567, 2004, Blackwell Publishing, Inc.

Lutsep et al., "Safety of Cortical Stimulation in Patients with Hemiparetic Stroke," Oasis, Online Abstract Submission and Invitation System - Program Planner, International Stroke Conference 2005, 1 page, American Stroke Association.

Misawa et al., "Low-frequency transcranial magnetic stimulation for epilepsia partialis continua due to cortical dysplasia;" Journal of the Neurological Sciences, vol. 234, 2005, pp. 37-39.

Motamedi et al., "Optimizing Parameters for Terminating Cortical Afterdischarges with Pulse Stimulation," Epilepsia 43(8):836-846, 2002, Blackwell Publishing, Inc.

The National Institutes of Health (NIH) Consensus Development Program, "Surgery for Epilepsy," National Institutes of Health Consensus Development conference Statement, Mar. 19-21, 1990, 16 pages.

Sioutos et al. Continuous Regional Cerebral Cortical Blood Flow Monitoring in Head-injured Patients, Neurosurgery, vol. 36, No. 5, May 1995, pp. 943-949.

Velasco et al. "Absolute and Relative Predictor Values of Some Non-Invasive and Invasive Studies for the Outcome of Anterior Temporal Lobectormy," Science Direct, vol. 31, Issue 1, Jan.-Feb. 2000, pp. 62-74, Elsevier Science, Inc.

Velasco et al., "Acute and Chronic Electrical Stimulation of the Centromedian Thalamic Nucleus: Modulation of Reticulo-Cortical Systems and Predictor Factors for Generalized Seizure Control," Archives of Medical Research, vol. 31, 2000, pp. 304-315, Elsevier Science, Inc.

Velasco et al., "Electrical Stimulation for Epilepsy: Stimulation of Hippocampal Foci," Stereotactic and Functional Neurosurgery, vol. 77, 2001, pp. 223-227.

Velasco et al., "Subacute and Chronic Electrical Stimulation of the Hippocampus on Intractable Temporal Lobe Seizures: Preliminary Report," Archives of Medical Research, vol. 31, 2000, pp. 316-328, Elsevier Science, Inc.

Velasco et al., "Subacute Electrical Stimulation of the Hippocampus Blocks Intractable Temporal Lobe Seizures and Paroxysmal EEG Activities," Epilepsia, vol. 41, No. 2, 2000, pp. 158-169, Lippincott Williams & Wilkins, Philadelphia.

Waxman et al., "The Interictal Behavior Syndrome of Temporal Lobe Epilepsy," Arch Gen Psychiatry, vol. 32, Dec. 1975, pp. 1580-1586.

Weinand et al., "Cerebral blood flow and temporal lobe epileptogenicity," J Neurosurg, Vol. 86, Feb. 1997, pp. 226-232.

Weinand et al., "Cerebral blood flow and temporal lobe epileptogenicity," Neurosurgical Focus, Nov. 1996, vol. 1, No. 5, AANS.ORG, http://www.aans.org/education/journal/neurosurgical/nov96/1-5-3.asp, 17 pages.

Weinand et al., Long-term ictal monitoring with subdural strip electrodes: prognostic factors for selecting temporal lobectomy candidates, J Neurosurg, vol. 77, 1992, pp. 20-28.

Weinand et al., "Surface cortical cerebral blood flow monitoring and single photon emission computed tomography; prognostic factors for selecting temportal lobectormy candidates," Seizure, vol. 3, 1994, pp. 55-59.

Weinand et al., "Targeted Subthreshold Cortical Stimulation for Recovery of Motor Hand Function following Hemiparetic Stroke," Abstract: Apr. 18, 2005, AANS.org, http://www.aans.org/Library/Article.aspx?Articleld=24934, 2 pages.

Yamamoto et al., "Low-frequency Electric Cortical Stimulation Has an Inhibitory Effect on Epileptic Focus in Mesial Temporal Lobe Epilepsy," Epilepsia, vol. 43, No. 5, 2002, pp. 291-295, Blackwell Publishing, Inc.

U.S. Appl. No. 11/697,694, filed Apr. 6, 2007, Fowler.

U.S. Appl. No. 11/697,696, filed Apr. 6, 2007, Pascual-Leone.

U.S. Appl. No. 11/697,703, filed Apr. 6, 2007, Gaw.

Mayberg, et al. "Deep Brain Stimulation for Treatment-Resistant Depression", Neuron, vol. 45, 651-660, Mar. 3, 2005, Copyright 2005.

Tyler, et al. "Audiological Rehabilitation of the Tinnitus Client",The Journal of the Academy of Rehabilitative Audiology, XXII, 1989, p. 30-42.

* cited by examiner

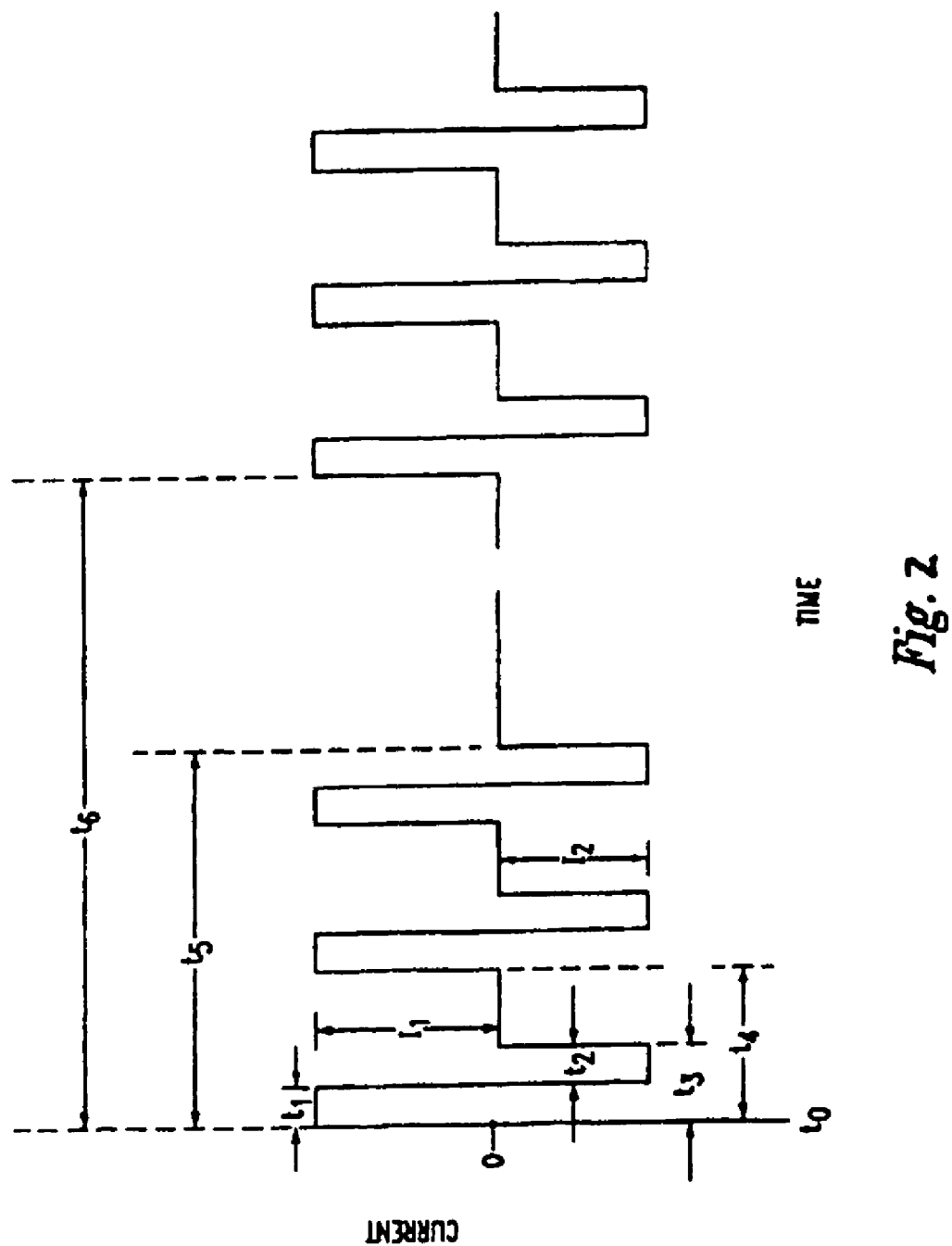

APPARATUS AND METHODS FOR APPLYING NEURAL STIMULATION TO A PATIENT

CROSS-REFERENCE TO RELATED APPLICATIONS

This application claims priority to pending U.S. Provisional Application No. 60/492,273, filed on Aug. 1, 2003, and incorporated herein in its entirety by reference.

INCORPORATION OF RELATED APPLICATIONS

This application is related to U.S. patent application Ser. No. 09/802,808 entitled "Methods and Apparatus for Effectuating a Lasting Change in a Neural-Function of a Patient," which claims the benefit of U.S. Provisional Application 60/217,981, filed Jul. 31, 2000, both of which are herein incorporated by reference. Additional applications are incorporated by reference in other portions of this application.

TECHNICAL FIELD

The present disclosure is related to systems and methods for applying stimulation to a target neural population within a patient, for example, a surface site on the patient's cortex.

BACKGROUND

A wide variety of mental and physical processes are controlled or influenced by neural activity in particular regions of the brain. The neural-functions in some areas of the brain (i.e., the sensory or motor cortices) are organized according to physical or cognitive functions, and various areas of the brain appear to have distinct functions in most individuals. In the majority of people, for example, the occipital lobes relate to vision, the left interior frontal lobes relate to language, and the cerebral cortex appears to be involved with conscious awareness, memory, and intellect.

Many problems or abnormalities can be caused by damage, disease and/or disorders in the brain. Effectively treating such abnormalities may be very difficult. For example, a stroke is a common condition that damages the brain. Strokes are generally caused by emboli (e.g., obstruction of a vessel), hemorrhages (e.g., rupture of a vessel), or thrombi (e.g., clotting) in the vascular system of a specific region of the brain. Such events generally result in a loss or impairment of a neural function (e.g., neural functions related to facial muscles, limbs, speech, etc.). Stroke patients are typically treated using various forms of physical therapy to rehabilitate the loss of function of a limb or another affected body part. Stroke patients may also be treated using physical therapy plus an adjunctive therapy such as amphetamine treatment. For most patients, however, such treatments are minimally effective and little can be done to improve the function of an affected body part beyond the recovery that occurs naturally without intervention.

Neurological problems or abnormalities are often related to electrical and/or chemical activity in the brain. Neural activity is governed by electrical impulses or "action potentials" generated in neurons and propagated along synaptically connected neurons. When a neuron is in a quiescent state, it is polarized negatively and exhibits a resting membrane potential typically between −70 and −60 mV. Through chemical connections known as synapses, any given neuron receives excitatory and inhibitory input signals or stimuli from other neurons. A neuron integrates the excitatory and inhibitory input signals it receives, and generates or fires a series of action potentials when the integration exceeds a threshold potential. A neural firing threshold, for example, may be approximately −55 mV.

It follows that neural activity in the brain can be influenced by electrical energy supplied from an external source such as a waveform generator. Various neural functions can be promoted or disrupted by applying an electrical current to the cortex or other region of the brain. As a result, researchers have attempted to treat physical damage, disease and disorders in the brain using electrical or magnetic stimulation signals to control or affect brain functions.

Transcranial electrical stimulation is one such approach that involves placing an electrode on the exterior of the scalp and delivering an electrical current to the brain through the scalp and skull. Another treatment approach, transcranial magnetic stimulation, involves producing a high-powered magnetic field adjacent to the exterior of the scalp over an area of the cortex. Yet another treatment approach involves direct electrical stimulation of neural tissue using implanted electrodes.

The neural stimulation signals used by these approaches may comprise a series of electrical or magnetic pulses directed toward affecting neurons within a target neural population. Stimulation signals may be defined or described in accordance with stimulation signal parameters including pulse amplitude, pulse frequency, duty cycle, stimulation signal duration, and/or other parameters. Electrical or magnetic stimulation signals applied to a population of neurons can depolarize neurons within the population toward their threshold potentials. Depending upon stimulation signal parameters, this depolarization can cause neurons to generate or fire action potentials. Neural stimulation that elicits or induces action potentials in a functionally significant proportion of the neural population to which the stimulation is applied is referred to as supra-threshold stimulation; neural stimulation that fails to elicit action potentials in a functionally significant proportion of the neural population is defined as sub-threshold stimulation. In general, supra-threshold stimulation of a neural population triggers or activates one or more functions associated with the neural population, but sub-threshold stimulation by itself does not trigger or activate such functions. Supra-threshold neural stimulation can induce various types of measurable or monitorable responses in a patient. For example, supra-threshold stimulation applied to a patient's motor cortex can induce muscle fiber contractions in an associated part of the body.

Although electrical or magnetic stimulation of neural tissue may be directed toward producing an intended type of therapeutic, rehabilitative, or restorative neural activity, such stimulation may result in collateral neural activity. In particular, neural stimulation delivered beyond a certain intensity, period of time, level, or amplitude can give rise to seizure activity and/or other types of collateral activity. It will be appreciated that certain types of collateral neural activity may be undesirable and/or inconvenient in a neural stimulation situation.

Another concern that arises in association with stimulating a surface site on a patient's cortex is conservation or minimization of applied power while operating a stimulation device. Various types of systems have an implanted pulse generator ("IPG") and an electrode assembly. The electrode assembly generally has a plurality of contacts that are carried by a common support member, such that the contacts are positionally fixed in close or generally close proximity relative to each other. In operation, the IPG delivers an electrical waveform to the electrode assembly, such that a first set of contacts provides a current delivery path and a second set of contacts provides a current return path. Thus, at any given time during waveform delivery, at least one contact has a positive bias and at least one contact has a negative bias, resulting in the generation of a bipolar field at the surface of the cortex within the area of the stimulation site. The bipolar field has a lower current density in the deeper layers of the cortex compared to the current density at the surface layers, and the bipolar field runs generally parallel to the cranium of the patient in the deeper layers of the cortex. Systems that generate a bipolar field at the stimulation site may require relatively high current levels to achieve an intended or desired therapeutic effect. This may result in increased power consumption, and possibly increase the likelihood of inducing collateral neural activity.

BRIEF DESCRIPTION OF THE DRAWINGS

FIG. 2 is a graph illustrating several parameters that may describe, define, or characterize a stimulation signal.

DETAILED DESCRIPTION

Figure 1:
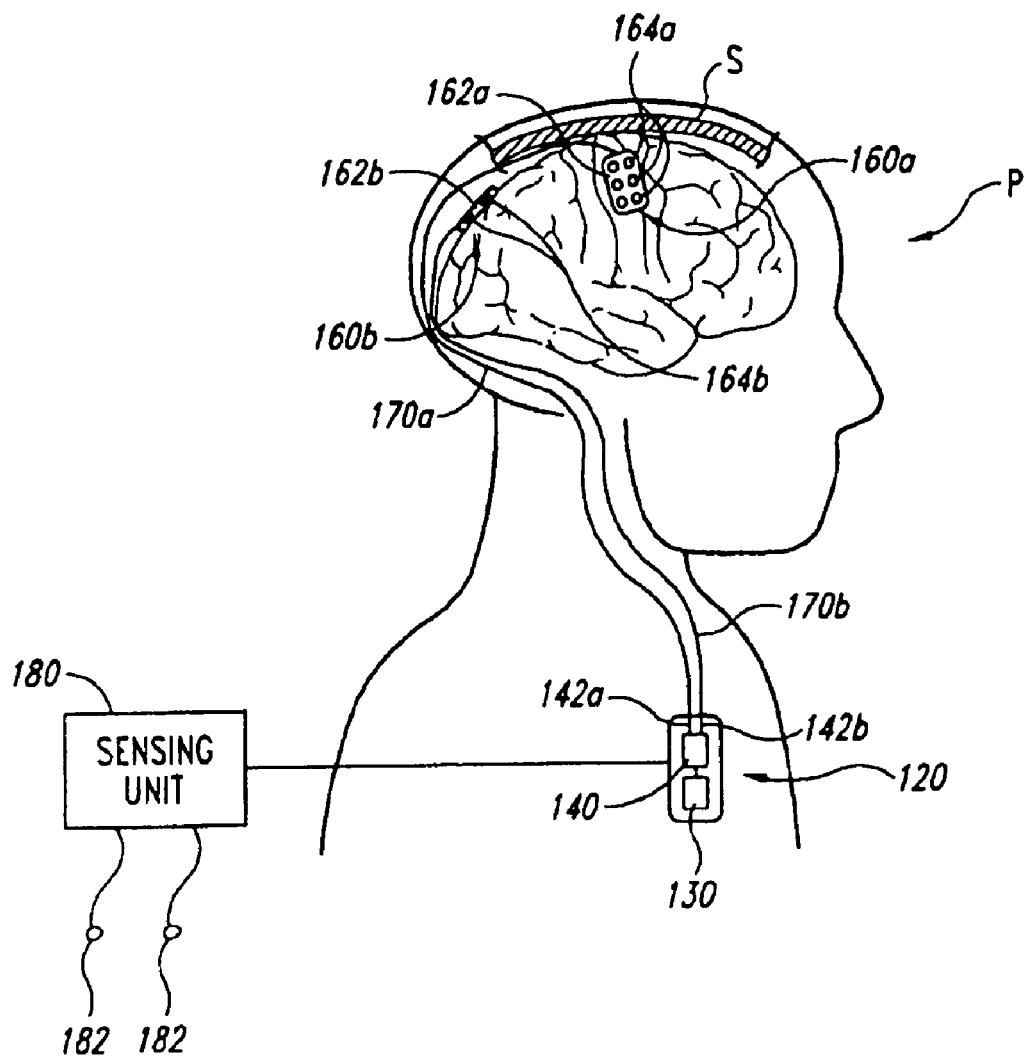
FIG. 1 is a side view of a system for applying electrical stimulation to a stimulation site on or proximate to the surface of the cortex of a patient in accordance with an embodiment of the invention.

The present disclosure describes systems and methods for neural stimulation that may enhance the efficacy and/or increase the efficiency of neural stimulation procedures. The neural stimulation may comprise a set of stimulation signals applied or delivered to or through target neural structures, target neural projections, and/or one or more target neural populations associated with controlling, influencing, or affecting one or more neurological functions under consideration. The neural stimulation may be directed toward facilitating and/or effectuating at least some degree of symptomatic relief and/or restoration or development of functional abilities in patients experiencing neurologic dysfunction arising from neurological damage, neurologic disease, neurodegenerative conditions, neuropsychiatric disorders, cognitive or learning disorders, and/or other conditions. Such neurologic dysfunction may correspond to Parkinson's Disease, essential tremor, Huntington's disease, stroke, traumatic brain injury, Cerebral Palsy, Multiple Sclerosis, a central pain syndrome, a memory disorder, dementia, Alzheimer's disease, an affective disorder, depression, bipolar disorder, anxiety, obsessive/compulsive disorder, Post Traumatic Stress Disorder, an eating disorder, schizophrenia, Tourette's Syndrome, Attention Deficit Disorder, an addiction, autism, epilepsy, a sleep disorder, a hearing disorder (e.g., tinnitis or auditory hallucinations), a speech disorder (e.g., stuttering), and/or one or more other disorders, states, or conditions.

For example, relative to controlling, influencing, stabilizing, restoring, enhancing, or gaining a motor function, a target neural population may comprise one or more portions of a patient's motor cortex. A neural location at which or a neural region in which stimulation signals are applied or delivered to or through a target neural population may be defined as a stimulation site. Thus, for a target neural population corresponding to the motor cortex, an exemplary stimulation site may comprise a location or region upon the patient's dura mater.

As another example, relative to controlling, influencing, stabilizing, restoring, or enhancing an auditory function, a target neural population may correspond to one or more portions of a patient's auditory cortex. A stimulation site may comprise an epidural or subdural cortical region that may facilitate the application, delivery, and/or transfer of stimulation signals to such a target neural population, for example, an epidural site adjacent or proximate to the Sylvian fissure. The application of unipolar stimulation signals to such a stimulation site in accordance with particular embodiments of the invention may increase a likelihood of affecting the target neural population in an intended manner.

A stimulation site may be identified in accordance with a variety of techniques, including (1) identification of one or more anatomical landmarks; (2) preoperatively (e.g., using Transcranial Magnetic Stimulation) and/or intraoperatively stimulating one or more brain locations to identify or map particular neural regions that induce or evoke a given type of patient response (for example, a movement or a sensation); (3) estimating a location at which the brain may recruit neurons to carry out a given type of neural activity that was previously performed by a damaged portion of the brain; (4) an electrophysiologic signal measurement and/or analysis procedure (e.g., acquisition and/or analysis of EEG, EMG, MEG, coherence, partial coherence, and/or other signals); and/or (5) a neural imaging procedure. In general, the number and/or location of stimulation sites under consideration may depend upon the nature, number, and/or extent of a patient's neurological condition and/or functional deficits.

Several embodiments of such systems and methods apply or deliver a unipolar, monopolar, or isopolar stimulation signal that may provide enhanced efficacy or efficiency stimulation using a low current level that reduces power consumption and/or mitigates collateral effects. Various embodiments of the present invention may apply or deliver neural stimulation at a subthreshold level or intensity, that is, at a level that raises or generally raises membrane potentials associated with a target neural population while avoiding the generation of a sufficient or statistically significant number of action potentials capable of triggering a neural function corresponding to the target neural population as a result of neural stimulation alone.

Stimulation systems and methods in accordance with the present invention may be used to treat various neurological conditions and/or facilitate particular types of neurological or functional patient outcomes. Depending upon the nature of a particular condition, neural stimulation applied or delivered in accordance with several embodiments of the invention may affect neural firing likelihoods and/or influence, facilitate, and/or effectuate reorganization of interconnections or synapses between neurons to (a) provide at least some degree of functional recovery and/or functional gain; and/or (b) develop one or more compensatory mechanisms to at least partially overcome a functional deficit or shortcoming. Such reorganization of neural interconnections may be achieved, at least in part, by a change in the strength of synaptic connections through a process that corresponds to a mechanism commonly known as Long-Term Potentiation (LTP). Neural stimulation applied or delivered in accordance with certain embodiments of the invention may alternatively or additionally affect particular neural populations through a process that corresponds to a mechanism commonly known as Long-Term Depression (LTD). Neural stimulation delivered or applied to one or more target neural populations either alone or in conjunction or association with one or more behavioral activities and/or other types of adjunctive or synergistic therapies (e.g., a drug or chemical substance therapy, a neurotrophic or growth factor therapy, and/or a cell implantation therapy) may facilitate, effectuate, or enhance therapeutic efficacy, for example, through neural plasticity and the reorganization of synaptic interconnections between neurons.

A. Systems for Applying Electrical Stimulation

FIG. 1 is a side view of a system for applying electrical stimulation to a neural stimulation site or region according to an embodiment of the invention. In various embodiments, the stimulation site may be upon, essentially upon, or proximate to the surface of the cortex of a patient P. The stimulation system may comprise a stimulus unit 120 and a patient interface that includes a set of electrodes, electrode arrangements and/or electrode assemblies 160 (hereinafter, "electrode assemblies"). In one embodiment, the set of electrode assemblies 160 includes a first electrode assembly 160a and a second electrode assembly 160b. Various alternate embodiments may include additional electrode assemblies, which may be positioned or implanted at or proximate to a set of stimulation sites, or remote from one or more stimulation sites. Electrode assemblies can stimulate different neural regions, e.g., regions carrying out different neural functions and/or regions carrying out neural functions at different locations of the body, including different extremities of the body.

Depending upon embodiment details, the system may also include a sensing unit 180 (shown schematically) configured to monitor one or more types of patient responses, activities, and/or behaviors. The sensing unit 180 may be further configured to communicate with the stimulus unit 120. The sensing unit 180 may include, for example, electrodes 182 and/or other devices (e.g., an accelerometer or motion detector) configured to sense a patient's neural activity (e.g., an EEG signal), neuromuscular activity (e.g., an EMG signal), behavioral activity (e.g., patient motion), and/or other types of patient activity.

The stimulus unit 120 generates and outputs stimulation signals, and the set of electrode assemblies 160 facilitates application or delivery of the stimulation signals to the patient P. The stimulus unit 120 may perform, direct, and/or facilitate neural stimulation procedures in a manner that enhances efficacy, mitigates a likelihood of inducing collateral neural activity, and/or conserves power, as described in detail below.

The stimulus unit 120 may comprise a pulse generator that is implanted into the patient P. In the embodiment shown in FIG. 1, the stimulus unit 120 is an IPG that is implanted in a thoracic, subclavicular, or abdominal location. In other embodiments, the stimulus unit 120 can be an IPG implanted in the patient's skull or just under the patient's scalp. For example, the stimulus unit 120 can be implanted above the patient's neckline at a location in or near the patient's cranium. Examples stimulus units 120 suitable for implantation in a patient's cranium are set forth in U.S. patent application Ser. No. 09/802,808 (previously incorporated by reference), as well as herein with reference to FIGS. 8A through 9B.

The stimulus unit 120 may comprise a controller 130 and a pulse system 140. The stimulus unit 120 may further comprise a power source, a battery, an energy storage device, and/or power conversion circuitry (not shown). The controller 130 may include a processor, a memory, and a programmable computer medium. The controller 130 may be implemented as a computer or a microcontroller, and the programmable medium may comprise software, instructions, and/or configuration information loaded into the memory and/or hardware that performs, directs, and/or facilitates neural stimulation procedures in accordance with one or more methods of the present invention.

The pulse system 140 generates and outputs stimulation signals. FIG. 2 is a graph illustrating several parameters that may describe, define, or characterize a stimulation signal. A stimulus start time $t_0$ may define an initial point at which a stimulation signal is applied to a target neural population. In one embodiment, the stimulation signal may be a symmetric or asymmetric biphasic waveform comprising a set or series of biphasic pulses, and which may be defined, characterized, or described by parameters including a pulse width $t_1$ for a first pulse phase; a pulse width $t_2$ for a second pulse phase; and a pulse width $t_3$ for a single biphasic pulse. The parameters can also include a stimulus repetition rate $1/t_4$ corresponding to a pulse repetition frequency; a stimulus pulse duty cycle equal to $t_3$ divided by $t_4$; a stimulus burst time $t_5$ that defines a number of pulses in a pulse train; and/or a pulse train repetition rate $1/t_6$ that defines a stimulus burst frequency. Other parameters include a peak current intensity $I_1$ for the first pulse phase and a peak current intensity $I_2$ for the second pulse phase. Those skilled in the art will understand that pulse intensity or amplitude may decay during one or both pulse phases, and a pulse may be a charge-balanced waveform. Those skilled in the art will further understand that in an alternate embodiment, pulses can be monophasic or polyphasic.

In certain embodiments, the pulse system 140 may generate and/or output stimulation signals in accordance with a theta burst pattern. In general, theta burst stimulation may comprise pulse bursts and/or pulse packets separated by quiescent intervals, such that the number of pulse packets per seconds corresponds or approximately corresponds to theta wave frequencies exhibited by the brain. In general, theta wave frequencies may range from approximately 3 to 10 Hz, and more particularly in certain embodiments, 4 to 8 Hz.

In particular embodiments, the pulse system 140 may vary and/or modulate stimulation signals in one or more manners, for example, in accordance with one or more mathematical operations and/or functions upon or corresponding to particular stimulation signal parameters. Exemplary manners of varying stimulation signals are described in detail in U.S. application Ser. No. 60/588,406, filed on Jul. 15, 2004, entitled "System and Method for Enhancing or Affecting Neural Stimulation Efficiency and/or Efficacy," incorporated herein by reference in its entirety.

The pulse system 140 may apply or output stimulation signals to, across, or between a first terminal 142a and a second terminal 142b. Since a stimulation signal may comprise a time-varying waveform, a relative polarity of the stimulation signal, and hence that of the first and second terminals 142a–b, may change or vary with time. With respect to outputting one or more stimulation signals having phases that differ in polarity, an anode may be defined as a terminal 142a–b to which a positive polarity phase within an initial pulse is first applied. For example, for a stimulation signal comprising a series of biphasic pulses where each pulse includes a positive polarity phase followed by a negative polarity phase, where positive and negative may respectively be defined relative to a zero potential level or a potential offset, an anode may be designated as the particular terminal 142a–b that first receives a positive polarity phase following the stimulus start time $t_0$. A cathode may be defined as a terminal 142a–b that provides electrical continuity for the stimulation signal delivered through the anodal terminal 142a–b. The polarity of the cathode may thus be opposite to that of the anode, or neutral. Depending upon embodiment details, a cathode may be defined as a terminal 142a–b to which a first negative polarity or lower potential phase within an initial pulse is first applied. Those skilled in the art will recognize that the terms anode and cathode could be defined in an opposite or different manner than as defined above, yet such opposite or different definitions would be equivalent, essentially equivalent, or consistent from a mathematical or circuit analysis perspective.

Depending upon embodiment details, (a) the first terminal 142a may be configured as an anode, while the second terminal 142b may be configured as a cathode; (b) the first terminal 142a may be configured as a cathode, while the second terminal 142b may be configured as an anode; or (c) the first and second terminals 142a–b may be selectively or programmably configured as an anode and a cathode, possibly in a predetermined, aperiodic, or pseudo-random time dependent manner. Such anode/cathode selectivity may occur on a sub-seconds-based, a seconds-based, an hours-based, and/or another type of time domain, and/or may be facilitated by signal selection circuitry (e.g., a multiplexor or a switch matrix) and/or redundant output circuitry within the stimulus unit 120. In particular embodiments, stimulus periods provided by the stimulus unit 120 can have durations of 30 seconds or less, 10 seconds or less, 2–5 seconds, about one second, and/or less than one second. The stimulus periods can include but are not limited to alternating cathodal and anodal periods, alternating unipolar periods, alternating bipolar periods, and/or periods that alternate between unipolar and bipolar. The electrical potential of the stimulation signal can also alternate between subthreshold levels and suprathreshold levels.

The first electrode assembly 160a may be positioned or implanted at a stimulation site that is located upon, essentially upon, or proximate to a target neural population upon, within, or near the patient's cerebral cortex. The first electrode assembly 160a may comprise a support member 162a and one or more contacts 164a carried by the support member 162a. The support member 162a may be configured for implantation at a stimulation site upon or at least proximate to the surface of the patient's cortex. The support member 162a, for example, can be a flexible or rigid substrate that is implanted under the cranium S such that the contacts 164a are positioned upon or adjacent to the dura mater at the stimulation site. In other embodiments, the support member 162a can be a portion of a cranial screw or a housing that is implanted through the cranium S, in a manner identical or analogous to that described in U.S. patent application Ser. No. 10/418,796, which is incorporated herein by reference.

The first electrode assembly 160a can have one or more contacts 164a arranged or positioned in a desired configuration. For example, the first electrode assembly 160a may include a single contact 164a, or a plurality of contacts 164a arranged as an array, grid, or other pattern. In the embodiment shown in FIG. 1, the first electrode assembly 160a also includes a first lead or link 170a that electrically couples some or all of the contacts 164a to the pulse system's first terminal 142a. The first electrode assembly 160a may therefore be configured as an anode or a cathode, in accordance with the anodal or cathodal configuration of the first terminal 142a of the pulse system 140. Contacts 164a that are not coupled to the first terminal 142a at a particular time may electrically float. The first link 170a may be a wired link or a wireless link. The first electrode assembly 160a can comprise a cortical neural-stimulation device, such as any of the devices described in U.S. patent application Ser. No. 09/802,808 (previously incorporated herein by reference), and U.S. patent application Ser. No. 10/418,976, which is also incorporated by reference herein.

The second electrode assembly 160b can be similar to the first electrode assembly 160a, or it can be a different type of electrode assembly. The second electrode assembly 160b may be positioned remotely from the first electrode assembly 160a. Since the second electrode assembly 160b provides electrical continuity with respect to the first electrode assembly 160a, the second electrode assembly 160b may be defined to reside at a circuit completion site. In the embodiment shown in FIG. 1, the second electrode assembly 160b comprises a separate electrode array including a support base 162b and one or more contacts 164b. In accordance with particular embodiment details, the support base 162b can be configured for positioning at (a) a location or site upon or proximate to the surface of the cortex spaced apart from the stimulation site where the first electrode assembly 160a is located; (b) a deep brain location; or (c) another area in the body above or below the neck. The second electrode assembly 160b can include a second link 170b that couples one or more contacts 164b (i.e., each contact 164b that is not electrically floating) to the second terminal 142b of the pulse system 140. Thus, the second electrode assembly 160b may be configured as an anode or a cathode, in accordance with the anodal or cathodal configuration of the pulse system's second terminal 142b.

In the embodiment shown, the second electrode assembly 160b, and more particularly the second electrode assembly's contacts 164b, are separate or otherwise detached from the first electrode assembly 160a. Thus, the second electrode assembly's contacts 164b are not attached to the first electrode assembly 160a, and the second electrode assembly's contacts 164b may be movable with respect to the contacts 164a of the first electrode assembly 164a before being implanted in the patient. The second electrode assembly 160b may accordingly be configured to be attached to or implanted in the patient at a location spaced apart from a stimulation site on or proximate to the cortex of the patient where electrical stimulation is to be applied to facilitate and/or effectuate a given neurological or neurofunctional outcome, such as neural plasticity or another type of neural reorganization corresponding to one or more neural populations.

In the embodiment shown in FIG. 1, each contact 164a of the first electrode assembly 160a that is coupled to the pulse system's first terminal 142a (i.e., each non-floating contact 164a) is biased in accordance with a first signal polarity. Thus, the pulse system 140 applies an identical polarity signal to each such contact 164a at any given time. Correspondingly, each intentionally biased or non-floating contact 164b of the second electrode assembly 160b is biased in accordance with a second signal polarity, where the second signal polarity is opposite or complementary to the first signal polarity, or neutral, to facilitate electrical current flow between the first and second electrode assemblies 160a–b.

Neural stimulation in which both an anode and a cathode are positioned, located, or situated within, essentially directly across, or proximate to a stimulation site may be defined as bipolar stimulation. In contrast, neural stimulation in which one of an anode and a cathode is positioned, located, or situated within or proximate to a stimulation site, while a respective corresponding cathode or anode is positioned, located, or situated remote from the stimulation site to provide electrical continuity may be defined as unipolar, monopolar, or isopolar stimulation. Thus, neural stimulation characterized by a biasing configuration in which an anode and a cathode are positioned, located, or situated in different neurofunctional areas or functionally distinct anatomical regions may be defined as unipolar stimulation. In a unipolar configuration, the pulse system 140 applies an identical polarity signal to each non-floating contact 162a–b positioned upon or proximate to a stimulation site. Unipolar stimulation may be defined as anodal unipolar stimulation when an anode is positioned upon or proximate to a stimulation site or a target neural population; and as cathodal unipolar stimulation when a cathode is positioned upon or proximate to a stimulation site or a target neural population.

In several embodiments, the second electrode assembly 160b is positioned apart or remote from the first electrode assembly 160a to establish an electric field that passes through deep layers of the cortex and/or other neural regions in a direction that is generally perpendicular or oblique with respect to (a) the first electrode assembly's contacts 164a; (b) the surface of the cortex under the first electrode assembly 160a; and/or (c) the cranium of the patient at or proximate to the stimulation site. The electric field, for example, is substantially normal to the first electrode assembly 160a in the deep layers of the cortex and/or other neural layers beneath the stimulation site.

Figure 3A:
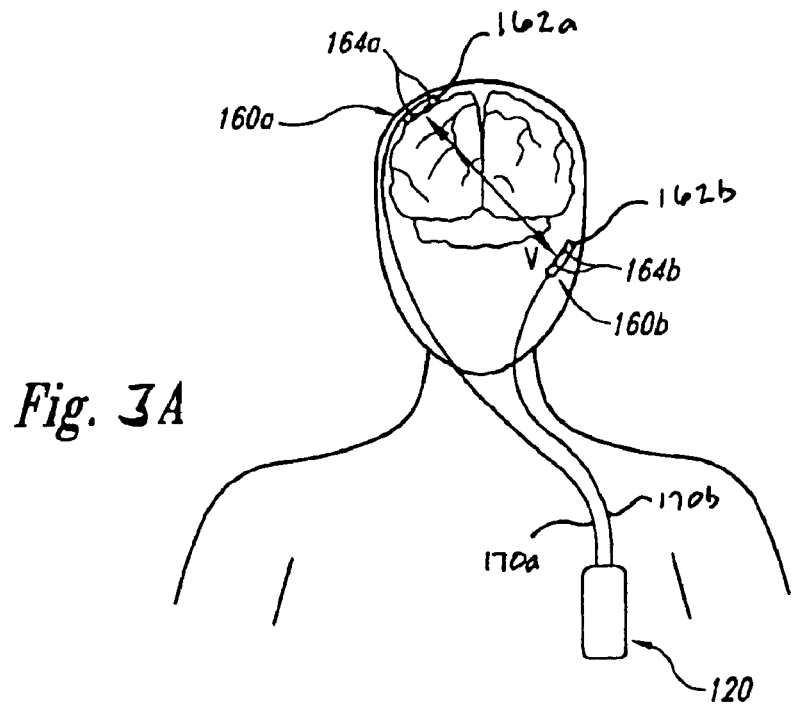
FIG. 3A is a front view of a system for applying electrical stimulation to a cortical stimulation site in accordance with FIG. 1A showing a different implementation of the system.
Figure 3B:
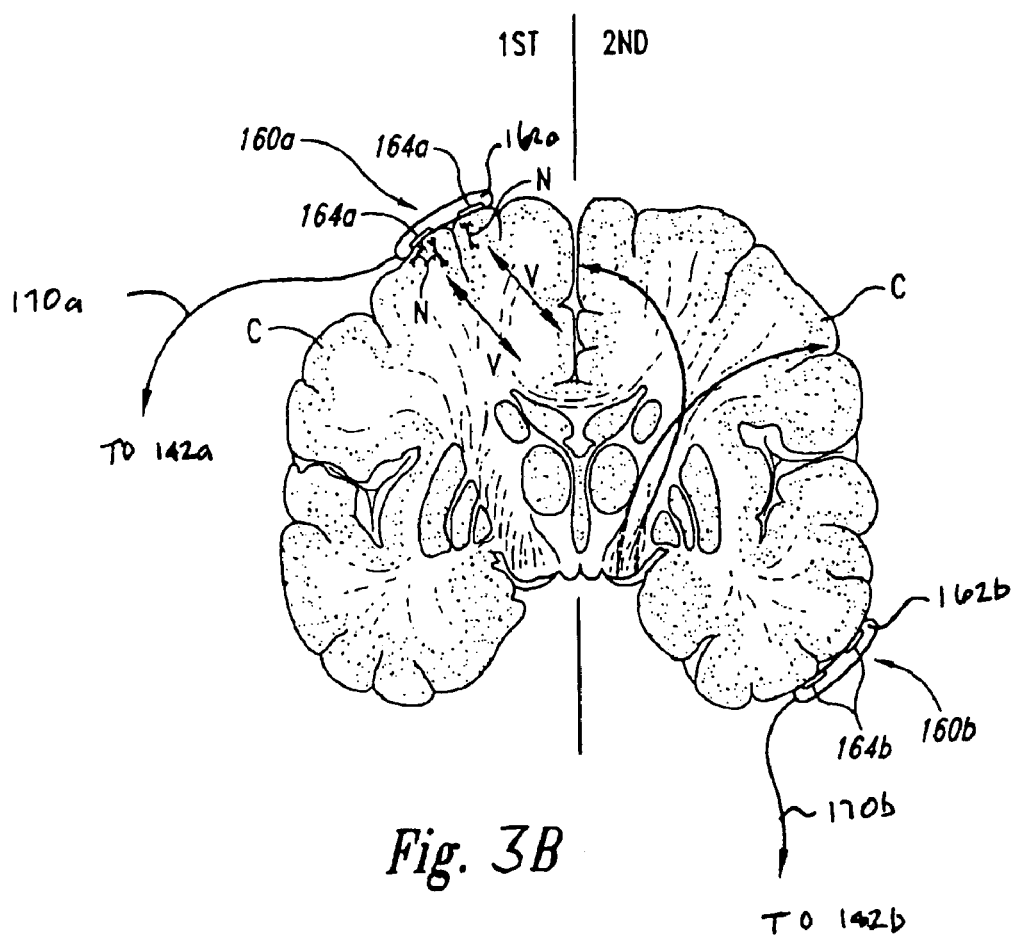
FIG. 3B is a cross-sectional view of a brain of a patient illustrating the implementation of FIG. 3A in greater detail.

FIGS. 3A and 3B illustrate a different implementation of a system for applying electrical stimulation to a neural stimulation site according to an embodiment of the invention. In this embodiment, a first electrode assembly 160a may be implanted in the patient at a stimulation site at least proximate to the surface of the cortex C (FIG. 3B) over target neurons or a target neural population N (FIG. 3B). A second electrode assembly 160b may be positioned at a location in the patient that is spaced apart from the stimulation site, for example, at a location that is above the patient's neck, to establish an electric field orientation or distribution that extends in a desired direction relative to the target neurons N. The second electrode assembly 160b may additionally or alternatively be positioned relative to other neural structures to minimize or mitigate collateral neural activity. The second electrode assembly 160b can be spaced apart from the patient's brain as shown in FIG. 3A, or the second electrode assembly 160b can be positioned at a different location of the patient's brain as shown in FIG. 3B.

The stimulus unit 120 may provide an output at a first polarity to the non-floating contacts 164a of the first electrode assembly 160a, and provide an output at a second polarity to the non-floating contacts 164b of the second electrode assembly 160b. The first electrode assembly's contacts 164a accordingly provide a unipolar, monopolar, or isopolar bias at the stimulation site upon or proximate to the patient's cortex C. The first polarity may be anodal or cathodal, and the second polarity may respectively be cathodal or anodal (i.e., opposite to the first polarity or neutral). A unipolar signal applied to the first electrode assembly's contacts 164a may establish an electric field that extends through deep layers of the cortex and/or other neural regions along a vector V extending generally perpendicular to, or at least oblique with respect to, the orientation of (a) the first electrode assembly 160a; (b) the surface of the cortex C at or proximate to the stimulation site; and/or (c) the cranium of the patient adjacent to the stimulation site (FIG. 3A).

Figure 3C:
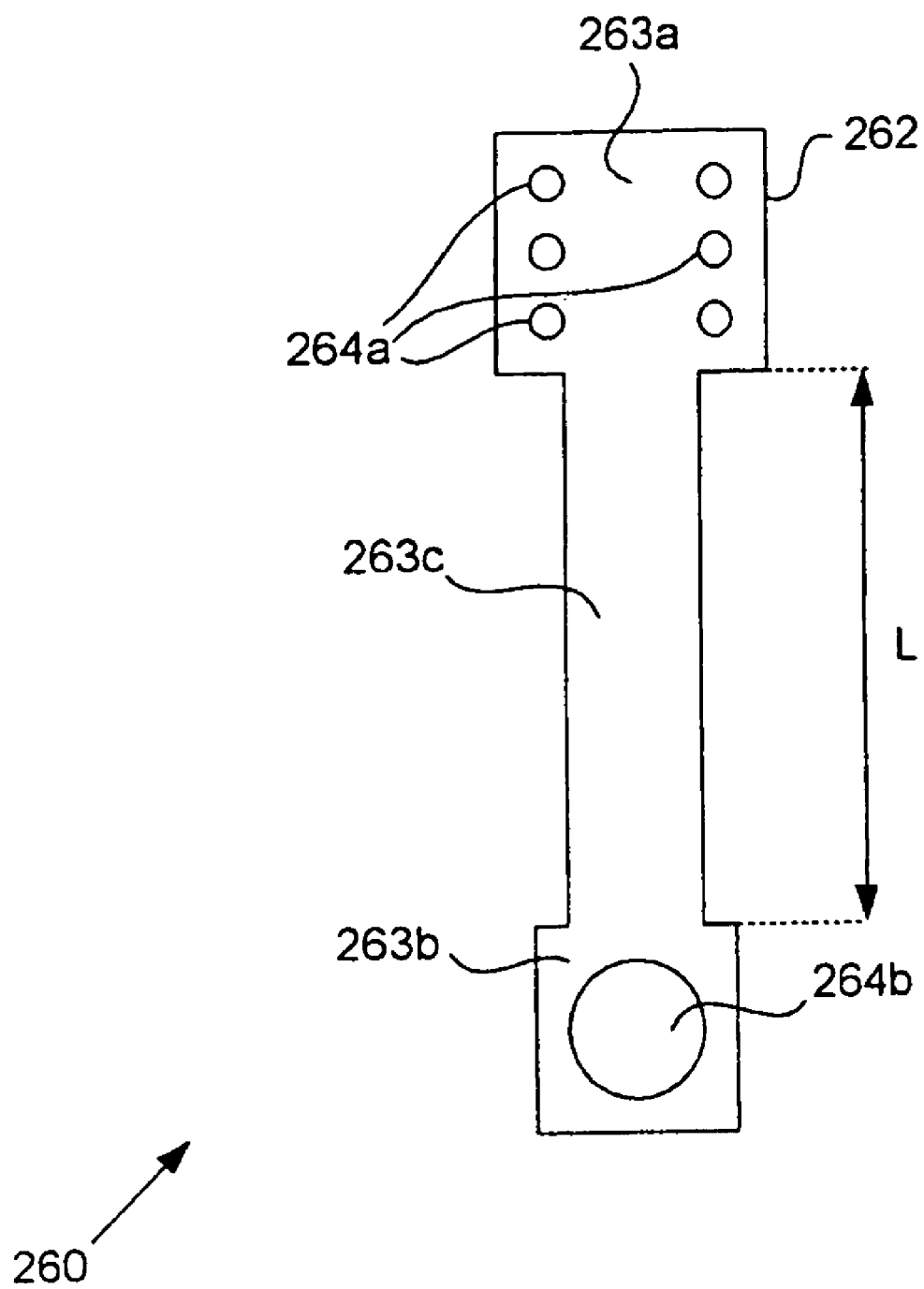
FIG. 3C is a schematic illustration of a combined electrode assembly that may be used to apply or deliver unipolar stimulation to a patient.

Certain systems and/or methods in accordance with the present invention may utilize or rely upon a single electrode assembly having a design that is suitable for providing unipolar stimulation rather than relying upon separate electrode assemblies. FIG. 3C is a schematic illustration of a combined electrode assembly 260 capable of applying or delivering unipolar stimulation to a patient. In one embodiment, the combined electrode assembly 260 includes a support member 262 having a local portion 263a, a remote portion 263b, and a separation portion 263c. The local portion 263a carries a first set of contacts 264a, and the remote portion 263b carries a second set of contacts 264b. The support member 262 may be formed from one or more flexible or generally flexible biocompatible materials (e.g., plastic and/or silicone), and the first and second sets of contacts 264a–b may be formed from one or more biocompatible conductive materials (e.g., Titanium and/or Platinum). Through appropriate couplings to a pulse system's first and second terminals 142a–b (for example, via a first and a second link 170a–b), the first set of contacts 264a may be configured as an anode or a cathode, while the second set of contacts 264b may respectively be configured as a cathode or an anode to facilitate unipolar stimulation.

The combined electrode assembly 260 may be implanted into a patient such that the local portion 263a resides at, upon, or proximate to a stimulation site, while the remote portion 263b resides at a circuit completion site that is distant or remote from the stimulation site. The separation portion 263c may have a length L that is sufficient to ensure that in a typical patient, an electric field generated at or in the vicinity of the local portion 263a is substantially perpendicular to the patient's cranium, cortical surface, and/or targeted neural tissues (which may include deep cortical layers or regions, as discussed below) beneath the stimulation site. In one embodiment, the value of L may be roughly an order of magnitude greater than the distance between the stimulation site and a target neural population or neural region that is deepest or farthest from the stimulation site. For subdural stimulation, an exemplary value of L may be roughly an order of magnitude or more greater than approximately 2.5 to 3.0 mm; and for epidural stimulation, an exemplary value of L may be roughly an order of magnitude greater than approximately 4.0 to 6.0 mm.

The location, depth, and/or spatial boundaries of target neural structures and/or a target neural population may depend upon the nature of a neurological condition or disorder under consideration. The extent to which an electric field reaches, penetrates, and/or travels into or through target neural structures and/or a target neural population may affect neural stimulation efficiency and/or efficacy. An electric field generated by unipolar stimulation may reach or penetrate deeper neural regions at a lower current level than an electric field generated by bipolar stimulation, as further described hereafter.

Figure 4:
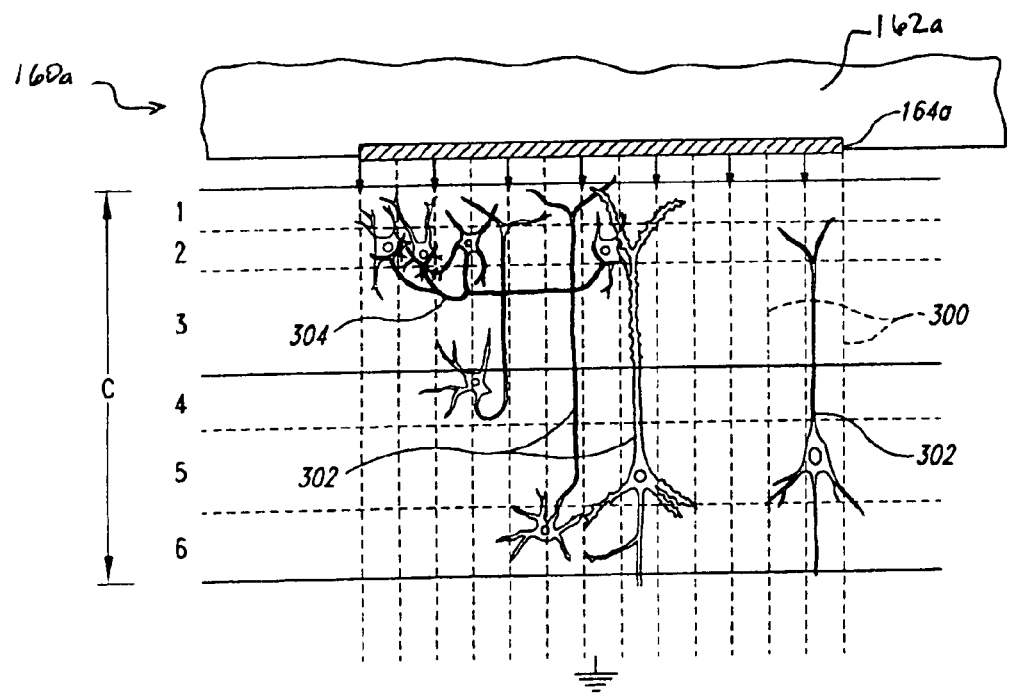
FIG. 4 is a schematic illustration showing an exemplary electric field distribution generated by unipolar electrical stimulation using a system for applying electrical stimulation to a cortical stimulation site in accordance with an embodiment of the invention.

FIG. 4 is a schematic illustration showing an exemplary electric field distribution generated by unipolar stimulation using a system in accordance with an embodiment of the invention. In FIG. 4, a first contact 164a is positioned at a stimulation site corresponding to a target neural population, while a second contact (not shown) is positioned distant or remote from the first contact 164a at a different neurofunctional or anatomical region. The first contact 164a may be biased as an anode, for example, and the second contact may be biased as a cathode to establish an electrical potential gradient or difference that facilitates the flow of electrical current (i.e., a net movement of charged particles or ions). A unipolar electric field distribution may be represented as a plurality of field lines 300 that extend through, for example, targeted deep layers of the cortex C and possibly other neural regions in a direction that is at least substantially perpendicular to (1) the surface of the cortex at or proximate to the stimulation site; and/or (2) the first electrode assembly's contacts 164a.

Figure 5:
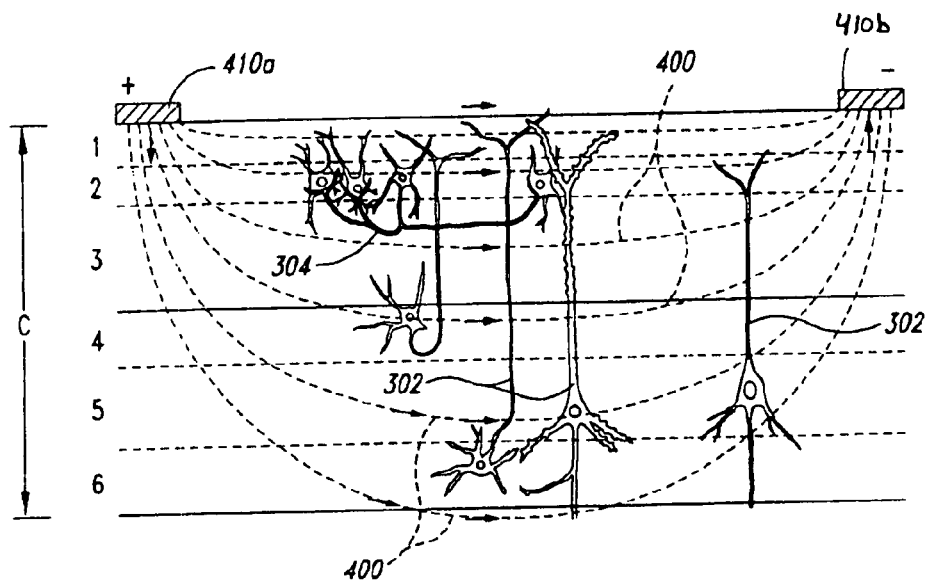
FIG. 5 is a schematic illustration showing an exemplary electrical field distribution generated by bipolar electrical stimulation at a cortical stimulation site.

FIG. 5 is a schematic illustration showing an exemplary electric field distribution generated by bipolar stimulation, which may be selectively produced in accordance with particular embodiments of the invention as further described below. In FIG. 5, a first contact 410a and a second contact 410b are configured to deliver bipolar stimulation to one or more portions of a target neural population. The first and second contacts 410a, 410b are located proximate to each other, within or upon a stimulation site that corresponds to the spatial extent of the target neural population. In a bipolar configuration, contacts 410a–b positioned at and/or near the stimulation site are biased at different polarities. In FIG. 5, the first contact 410a is biased as an anode, while a second contact 410b is biased as a cathode. A bipolar electric field distribution may be represented as a plurality of field lines 400 having field components that are generally parallel to (1) the surface of the cortex at or proximate to the stimulation site; and/or (2) a support member (not shown) configured to carry the first and second contacts 410a–b.

In general, an electrical potential gradient or difference between an anode and a cathode configured to provide unipolar stimulation exists over a longer or greater distance than an electrical potential gradient between an anode and a cathode configured to provide bipolar stimulation. Thus, an anode to cathode electrical current pathway associated with unipolar stimulation will typically be longer than an electrical current pathway associated with bipolar stimulation. Unipolar stimulation may therefore provide a greater degree of therapeutic efficacy than bipolar stimulation when stimulation of neural regions, structures, and/or projections that are deeper or more distant than those just beneath and/or in the near vicinity of the stimulation site may be of importance. Moreover, unipolar stimulation may deliver more current to such deeper or more distant neural regions at a lower power level than bipolar stimulation, which may result in greater stimulation efficiency and/or a reduced likelihood of inducing collateral neural activity. Enhanced stimulation efficiency may be important when treating chronic, near-chronic, and/or longer-term conditions, for example, movement disorders or central pain syndrome.

In addition to or association with the foregoing, an electric field polarity, orientation and/or distribution relative to particular types of neurons, neural projections, neural structures, and/or neurofunctional regions may influence or affect neural stimulation efficiency and/or efficacy. The cortex C may be organized as a set of 6 layers, where layer 1 maintains a boundary corresponding to the cortical surface. Successive cortical layers exist or reside at increasing depths relative to the cortical surface. Thus, layer 6 corresponds to a deepest cortical layer. The thickness or extent of any given cortical layer, and the type, number, and/or size of neurons, neural projections, and/or neural structures therein depends upon the cortical neurofunctional region under consideration.

Neurons convey input signals along their dendrites toward their cell bodies. Neurons in the cortex C include pyramidal cells 302 and interneurons 304. In the motor cortex, the largest pyramidal cells 320 have soma or cell bodies that reside in deep cortical layer 5. Pyramidal cells 302 have dendrites that project away from their cell bodies into overlying or superficial cortical layers, toward the cortical surface in a manner that is approximately perpendicular or normal to the layer structure of the cortex C. Interneurons 304 have cell bodies that commonly reside in cortical layers 2, 3, and 4, and include dendrites that tend to project away from their cell bodies within the same layer or into an adjacent layer in a manner that is generally lateral or parallel with respect to the layer structure of the cortex C.

An optimal, near optimal, or desirable electric field orientation for therapeutic neural stimulation may be based upon or determined by the orientation of one or more types of neurons, neural structures, and/or neural projections within or associated with a target neural population N. For example, an electric field that is oriented generally parallel to a main or overall direction in which pyramidal cell dendrites project, that is, generally perpendicular or normal to the cortical layer structure (or equivalently, generally perpendicular or normal to the surface of the cortex C or the cranium), may preferentially influence or exert a more significant effect upon pyramidal cells 302 than interneurons 304, which include dendrites that generally project lateral to the cortical layer structure. In an analogous manner, an electric field that is oriented generally parallel to a typical or overall direction in which interneuron dendrites project, that is, generally parallel or lateral to the cortical layer structure, may preferentially influence or exert a more significant effect upon interneurons 304 than pyramidal cells 302.

In view of the foregoing, systems and/or methods in accordance with particular embodiments of the invention may apply or deliver stimulation signals having one or more polarities that may enhance a likelihood of facilitating or effectuating a desired neurological and/or functional outcome based upon the types of neurons, neural structures, and/or neural projections involved in subserving such an outcome. For example, specific embodiments of the invention may apply unipolar stimulation at one or more times to patients experiencing certain types of central pain syndrome. As another example, various embodiments of the invention may apply unipolar stimulation, possibly in conjunction with a behavioral therapy, to patients having functional deficits associated with stroke, traumatic brain injury, cerebral palsy, and/or other disorders (e.g., tinnitus). In certain situations, unipolar stimulation may more effectively facilitate or effectuate neural disinhibition and/or neuroplastic change associated with a target neural population than bipolar stimulation, thereby enhancing the extent to which such patients can recover lost functional abilities and/or develop new abilities.

Unipolar stimulation may facilitate or effectuate enhanced recovery or development of functional abilities in patients experiencing particular types of neurologic dysfunction when compared to bipolar stimulation. For example, cathodal unipolar stimulation in conjunction or association with a behavioral therapy such as an Activity of Daily Living (ADL) may facilitate or effectuate a greater degree of functional development and/or recovery in a patient experiencing functional deficits associated with stroke, traumatic brain injury, and/or neurological damage than bipolar stimulation either alone or in association or conjunction with such a behavioral therapy. Moreover, such enhanced recovery may occur using lower current or average power levels than would be required for bipolar stimulation, thereby conserving power and/or reducing a likelihood of inducing collateral neural activity.

Certain systems and/or methods in accordance with the invention may deliver unipolar stimulation during a unipolar stimulation period and bipolar stimulation during a bipolar stimulation period. For example, relative to facilitating or effectuating neuroplasticity, both pyramidal cells 302 and interneurons 304 may play a role in neural reorganization. Thus, a system and/or method may deliver unipolar stimulation to more selectively influence or affect pyramidal cells 302 during a unipolar stimulation period, and deliver bipolar stimulation to more selectively influence or affect interneurons 304 during a bipolar stimulation period. One or more unipolar and/or bipolar stimulation periods may be identical or different in duration, and may occur in a successive or generally successive manner, with or without one or more types of intervening delays, interruptions, or cessations. Any given unipolar stimulation period, bipolar stimulation period, and/or interruption period between unipolar and/or bipolar stimulation periods may correspond to a subseconds-based, a seconds-based, an hours-based, and/or another type of time domain. Depending upon embodiment details, alternation between unipolar and/or bipolar stimulation periods and/or intervals between such periods may temporally occur in a predetermined, aperiodic, or pseudo-random manner. Neural stimulation may be delivered during one or more unipolar and/or bipolar stimulation periods in conjunction or association with one or more adjunctive or synergistic therapies, for example, a behavioral therapy and/or a drug therapy. An adjunctive therapy corresponding to a unipolar stimulation period may be identical to or different from an adjunctive therapy corresponding to a bipolar stimulation period.

In cortical regions associated with motor control, pyramidal cell axons that project into the spinal cord, brain stem, basal ganglia, and/or other areas may serve as cortical outputs involved in facilitating or controlling movement. In view of manners in which pyramidal cell dendrites and axons project as described above, a given type of unipolar neural stimulation may elicit or generate a patient response or movement at a different (e.g., lower) current level or intensity than bipolar stimulation. Thus, unipolar stimulation may provide or induce an intended or desired effect at a lower current level than bipolar stimulation, thereby conserving power and/or reducing a likelihood of inducing collateral activity. Similarly, unipolar stimulation may facilitate determination of a therapeutic current level using lower amplitude test stimulation signals than required by bipolar stimulation. In some embodiments, a therapeutic current level corresponding to a given type of unipolar stimulation may be mapped to a therapeutic current level that corresponds to a different type of unipolar stimulation and/or bipolar stimulation in accordance with a mapping function and/or empirical data.

In addition to the foregoing, certain types of neural cells may exhibit different types of signal conductance properties based upon whether the motion of electrical charges or electrically charged particles (i.e., ions) is toward or away from the axon hillock, the initial axonal region proximate to the cell body through which dendritic inputs are integrated. For instance, in pyramidal cells 302, intracellular ions diffusing toward the axon hillock experience a lower impedance than intracellular ions diffusing toward the dendritic tree, thereby giving rise to an intracellular differential impedance (Neurophysiological Techniques: Applications to Neural Systems, Neuromethods 15, Eds. A. A. Boulton, G. B. Baker, and C. H. Vanderwolf). As a result, anodal unipolar stimulation may affect or influence a neural population, neural structures, and/or neural projections differently than cathodal unipolar stimulation.

Stimulation signal polarity characteristics may influence or affect an extent to which and/or a manner in which particular neural structures experience a potential difference and/or depolarization or polarization relative to each other, which may affect neural stimulation efficacy and/or efficiency. For example, due to the existence of a potential gradient between a cathode and an anode, a relative dendrite to axon hillock or axon depolarization or hyperpolarization state may give rise to neural stimulation efficacy differences between cathodal unipolar stimulation and anodal unipolar stimulation.

During cathodal unipolar stimulation, a negative first pulse phase applied at a stimulation site may give rise to an intracellular concentration of positive ions, thereby shifting the electrical state of proximate dendrites toward a more depolarized state than, for example, axon hillocks corresponding to such dendrites.

In an analogous manner, during anodal unipolar stimulation, a positive first pulse phase applied at a stimulation site may give rise to an enhanced intracellular concentration of negative ions, thereby shifting the electrical state of such dendrites toward a more hyperpolarized state than axon hillocks corresponding to such dendrites.

A dendritic potential shift toward a more depolarized state and/or a more hyperpolarized state may affect dendritic signal processing and/or signal generation and/or signal transfer mechanisms. Such a potential shift may affect neural stimulation efficacy, for example, by influencing an extent to and/or manner in which postsynaptic dendrites react or respond to and/or process presynaptic input.

In certain neural stimulation situations directed toward facilitating and/or effectuating neural plasticity, cathodal unipolar stimulation may increase a likelihood that dendrites within a target neural population respond to and/or process neurofunctionally relevant synaptic input in a manner that enhances a likelihood of generating action potentials that may subserve the development and/or recovery of one or more functional abilities. Neurofunctionally relevant synaptic input may arise from or correspond to an adjunctive or synergistic therapy, for example, a behavioral therapy. The aforementioned neural stimulation situations may include, for example, neural stimulation directed toward rehabilitation of patients experiencing symptoms associated with neurological damage (e.g., arising from stroke or traumatic brain injury), neurodegenerative disorders (e.g., Parkinson's disease, Alzheimer's disease), neuropsychiatric disorders (e.g., depression, OCD), and/or other types of neurologic dysfunction.

In general, anodal or cathodal unipolar stimulation may be more efficacious and/or efficient than cathodal or anodal unipolar stimulation, respectively, or bipolar stimulation in the context of particular neural stimulation situations, which may include, for example, neural stimulation directed toward traumatic brain injury, cerebral palsy, movement disorders, central pain syndrome, tinnitus, neuropsychiatric disorders, auditory hallucinations, and/or other conditions.

In particular neural stimulation situations, a likelihood of realizing a given type of neurofunctional outcome may be enhanced through multiple anodal unipolar, cathodal unipolar, and/or bipolar stimulation procedures, which may be applied in a simultaneous, alternating, and/or varying manner. Such stimulation procedures may correspond to identical, generally identical, or different stimulation sites and/or stimulation parameters (e.g., pulse repetition frequency, first phase pulse width, a peak current and/or voltage amplitude or magnitude, theta burst characteristics, a waveform variation and/or modulation function, and/or other parameters) depending upon the nature of a patient's neurologic dysfunction, patient condition, and/or embodiment details. Moreover, any given stimulation procedure and/or an interval between stimulation procedures may correspond to a subseconds-based, a seconds-based, an hours-based, and/or another type of time period or domain. In one embodiment, before, during, and/or after one or more portions of a cathodal stimulation procedure directed toward a first target neural population, an anodal unipolar stimulation procedure may be directed toward a second target neural population. The first and second target neural populations may reside in the same or different brain hemispheres.

Figure 6:
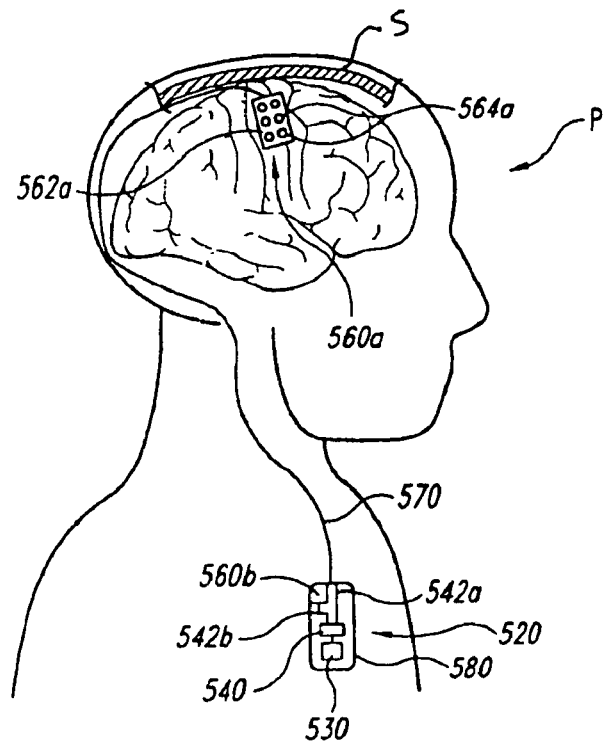
FIG. 6 is a side view of a system for applying electrical stimulation to a cortical stimulation site in accordance with another embodiment of the invention.

FIG. 6 is a side view of a system for applying electrical stimulation to a surface site on the cortex in accordance with an embodiment of the invention. In this embodiment, the system includes a stimulus unit 520 and a patient interface including a first electrode assembly 560a and a second electrode assembly 560b. The stimulus unit 520 can include a controller 530 and a pulse system 540 similar to the controller 130 and pulse system 140 of the stimulation unit 120 described above with reference to FIG. 1. The stimulus unit 520 can also include a housing 580 that is configured to be implanted or otherwise attached to the patient.

The first electrode assembly 560a can be similar to the first electrode assembly 160a described above with reference to FIG. 1. The first electrode assembly 560a can accordingly include a support member 562a configured to be implanted proximate to the cortex of the patient and at least one surface contact 564a. The surface contacts 564a can be coupled to a first terminal 542a of the stimulus unit 520 by a link 570.

The second electrode assembly 560b can be a separate item or element attached to the stimulus unit 520, or the second electrode assembly 560b can be an integral component of the stimulus unit 520. The second electrode assembly 560b, for example, can be a conductive portion of the housing 580 of the stimulus unit 520. In other embodiments, the entire housing 580 of the stimulus unit 520 can be a conductive material that defines the second electrode assembly 560b, or a portion of the housing 580 can be covered with an appropriate type of dielectric or insulating material or be composed of such a material to limit the conductive surface area of the second electrode assembly 560b to a desired shape or area. In still other embodiments, the second electrode assembly 560b is a separate set of contacts attached to the housing 580. The second electrode assembly 560b is coupled to a second terminal 542b of the pulse system 540.

The system shown in FIG. 6 operates by electrically biasing the surface contacts 564a at an identical polarity, and biasing the second electrode assembly 560b with an opposite or neutral polarity. For example, the system may be configured to deliver anodal unipolar stimulation to a stimulation site by biasing the surface contacts 564a as an anode, and biasing the second electrode assembly 560b as a cathode. It will be appreciated that the surface contacts 564a could alternatively be biased as a cathode while the second electrode assembly 560b is biased as an anode. The system shown in FIG. 6 accordingly provides a unipolar signal at the stimulation site on or proximate to the surface of the cortex of the patient.

Another aspect of the invention may involve configuring a neural stimulation system to induce a desired electrical field and/or current density at or proximate to a stimulation site as well as a remote circuit completion site. In one embodiment, the aggregate surface area of conductive surfaces that provide circuit completion or electrical continuity remote or generally remote from the stimulation site (e.g., contacts 164b carried by a second electrode assembly 160b or 560b, or an exposed conductive surface of a housing 580) is approximately 200%–1500% of the aggregate surface area of conductive surfaces that apply or deliver stimulation signals to one or more stimulation sites (e.g., contacts 164a or 564a carried by a first electrode assembly 160a or 560a), and more specifically 250%–450%. The larger conductive surface area corresponding to the circuit completion site reduces the current density at the current completion site compared to the stimulation site; this is expected to reduce collateral neural activity, muscle activity, and/or patient sensation in the region of the circuit completion site.

Figure 7:
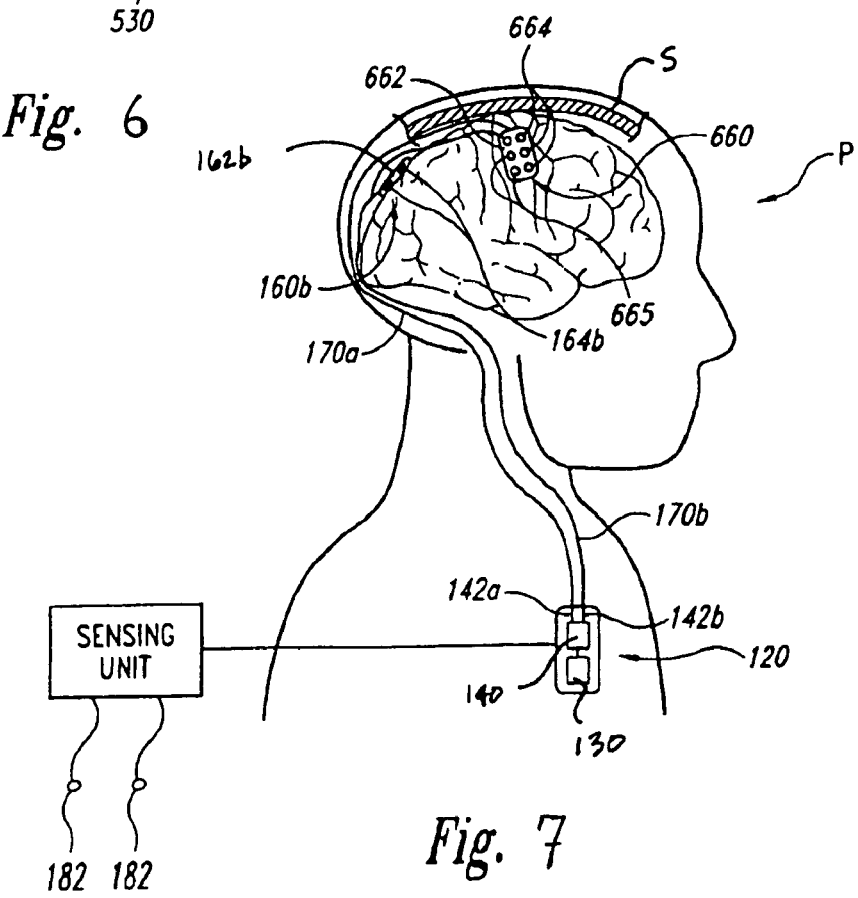
FIG. 7 is a side view of a system for applying electrical stimulation to a cortical stimulation site in accordance with another embodiment of the invention.

FIG. 7 is a side view illustrating a system for applying electrical stimulation to a surface site on the cortex in accordance with another embodiment of the invention. In this embodiment, the system includes the stimulus unit 120, the second electrode assembly 160b, and a surface electrode assembly 660. The surface electrode assembly 660 can comprise an array including a support member 662 configured to be implanted at the cortical stimulation site, a plurality of first surface contacts 664 carried by one portion of the support member 662, and a plurality of second surface contacts 665 carried by another section of the support member 662. The first surface contacts 664 are coupled to the first link 170a to electrically couple the first surface contacts 664 to the first terminal 142a of the stimulus unit 120. The second surface contacts 665 can be coupled to the second link 170b to electrically couple the second surface contacts 665 to the second terminal 142b of the stimulus unit 120. The first surface contacts 664 can be biased as an anode, and the second surface contacts 665 can be biased as a cathode, or vice versa. In an alternate embodiment, the second surface contacts 665 can be connected to a separate link to be coupled to a third terminal of the stimulus unit 120. The second surface contacts 665 can accordingly be biased independently of either the first surface contacts 664 or the second electrode assembly's contacts 164b.

The embodiment of the system illustrated in FIG. 7 can provide a combination of unipolar and bipolar stimulation. For example, the first surface contacts 664 can be biased at a first polarity while the second surface contacts 665 or the return contacts 164b are biased at a second polarity. In another embodiment, the second surface contacts 665 are coupled to another terminal on the stimulus unit 120 so that the second surface contacts 665 can be biased separately from the return contacts 164b. This particular embodiment operates in a manner in which the first surface contacts 664 and the second electrode assembly's contacts 164b can be biased while not biasing the second surface contacts 665 during a unipolar stimulation period, and then the first surface contacts 664 can be biased at the first polarity while the second surface contacts 665 are biased at the second polarity during a bipolar stimulation period. The stimulus unit 120 can alternate unipolar stimulation and bipolar stimulation periods according to a desired sequence to provide a combination of unipolar and bipolar stimulation.

Figure 8A:
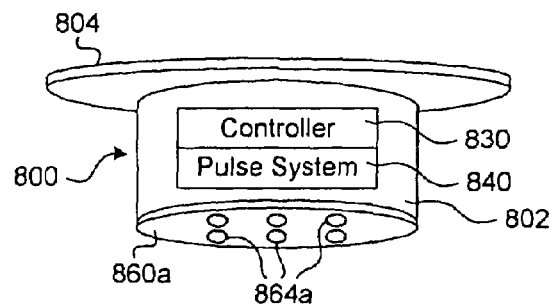
FIGS. 8A and 8B are an isometric view and a cross sectional view, respectively, of a system for applying electrical stimulation to a site on or proximate to the cortex in accordance with another embodiment of the invention.
Figure 8B:
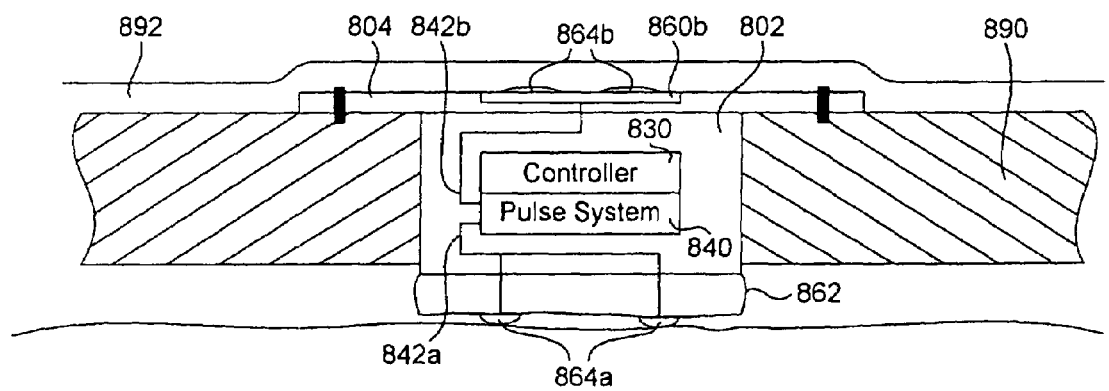

FIG. 8A is an isometric view and FIG. 8B is a cross sectional view of a system for applying electrical stimulation to a surface site on or proximate to the cortex in accordance with another embodiment of the invention. In one embodiment, the system comprises a support member 800 that may carry a control unit 830 and a pulse system 840, plus a first electrode assembly 860a and a second electrode assembly 860b. The support member 800 may include a housing 802 configured for implantation into the skull 890, and an attachment element 804 configured for connection to the skull 890 by fasteners, an adhesive, and/or an anchor.

The first electrode assembly 860a may comprise a biasing element 862 that carries a first set of electrical contacts 864a. The biasing element 862 may be formed using a soft, conformable, and/or compressible biocompatible material. In one embodiment, the first electrode assembly 860a is coupled to a first terminal 842a of the pulse system 840. The second electrode assembly 860b may comprise one or more exposed conductive portions of the housing 802 and/or the attachment element 804, and/or a second set of electrical contacts 864b that are carried by the housing 802 and/or the attachment element 804. The second electrode assembly 860b may be coupled to a second terminal 842b of the pulse system 840. Depending upon embodiment details, the pulse system's first and second terminals 842a–b may be configured as an anode and a cathode, possibly in a selectable or programmable manner. Additionally, configuration or establishment of an anodal and a cathodal relationship between the pulse system's first and second terminals 842a–b may occur in a predetermined, aperiodic, or pseudo-random time-varying manner.

The support member 800 may be implanted into or through a craniotomy that is above a stimulation site, such that one or more portions of the biasing element 862 and/or the first set of contacts 864a reside upon, essentially upon, or proximate to the stimulation site. Following implantation, the attachment element 804 may be covered by the patient's scalp 892. The first electrode assembly 860a may be biased in accordance with a first polarity to apply or deliver unipolar stimulation to a target neural population, neural projections, and/or neural structures associated with the stimulation site. The second electrode assembly 860b may be biased in accordance with a second polarity to provide electrical continuity for stimulation signals delivered by the first electrode assembly 860a. In such a configuration, an electrical current pathway between the first and second electrode assemblies 842a–b may include one or more portions of the patient's cortex, one or more neural regions below the cortex, vasculature, and/or portions of the patient's scalp. In order to eliminate, essentially eliminate, or minimize electrical current flow from the first electrode assembly 860a to the second electrode assembly 860b along a current path that includes an interface between the skull 890 and the edge of the housing 802 and/or the attachment element 804, one or more portions of the housing 802 and/or the attachment element 804 may comprise or include an insulating material that forms a nonconductive seal or barrier between the skull 890 and the housing 802 and/or the attachment element 804.

Figure 8C:
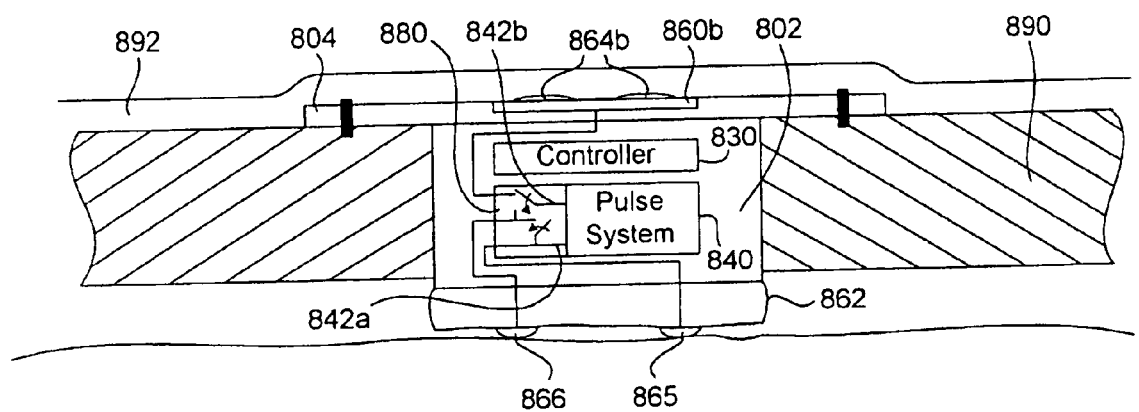
FIG. 8C is a cross sectional view of a system for applying electrical stimulation to a site on or proximate to the cortex according to another embodiment of the invention.

FIG. 8C is a cross sectional view of a system for applying electrical stimulation to a surface site on or proximate to the cortex according to another embodiment of the invention. Relative to FIGS. 8A and 8B, like reference numbers indicate like elements. In the embodiment shown in FIG. 8C, the first electrode assembly 860a includes a first subset of contacts 865 coupled to the pulse system's first terminal 842a. Additionally, the pulse system 840 includes a signal selection module 880 capable of selectively coupling (1) a second subset of contacts 866 to the first or second terminal 842a–b of the pulse system 830; and/or (2) the second electrode assembly 860b to the pulse system's second terminal 842b (in a manner that avoids simultaneous coupling of the second subset of contacts 866 to the first and second terminals 842a–b). The embodiment shown in FIG. 8C may thus be configured to provide unipolar stimulation by biasing the first subset of contacts 865 and possibly the second subset of contacts 866 at a first polarity, and biasing the second electrode assembly 842b at a second polarity; or bipolar stimulation by biasing the first subset of contacts 865 at a first polarity and the second subset of contacts 866 at a second polarity.

Figure 9A:
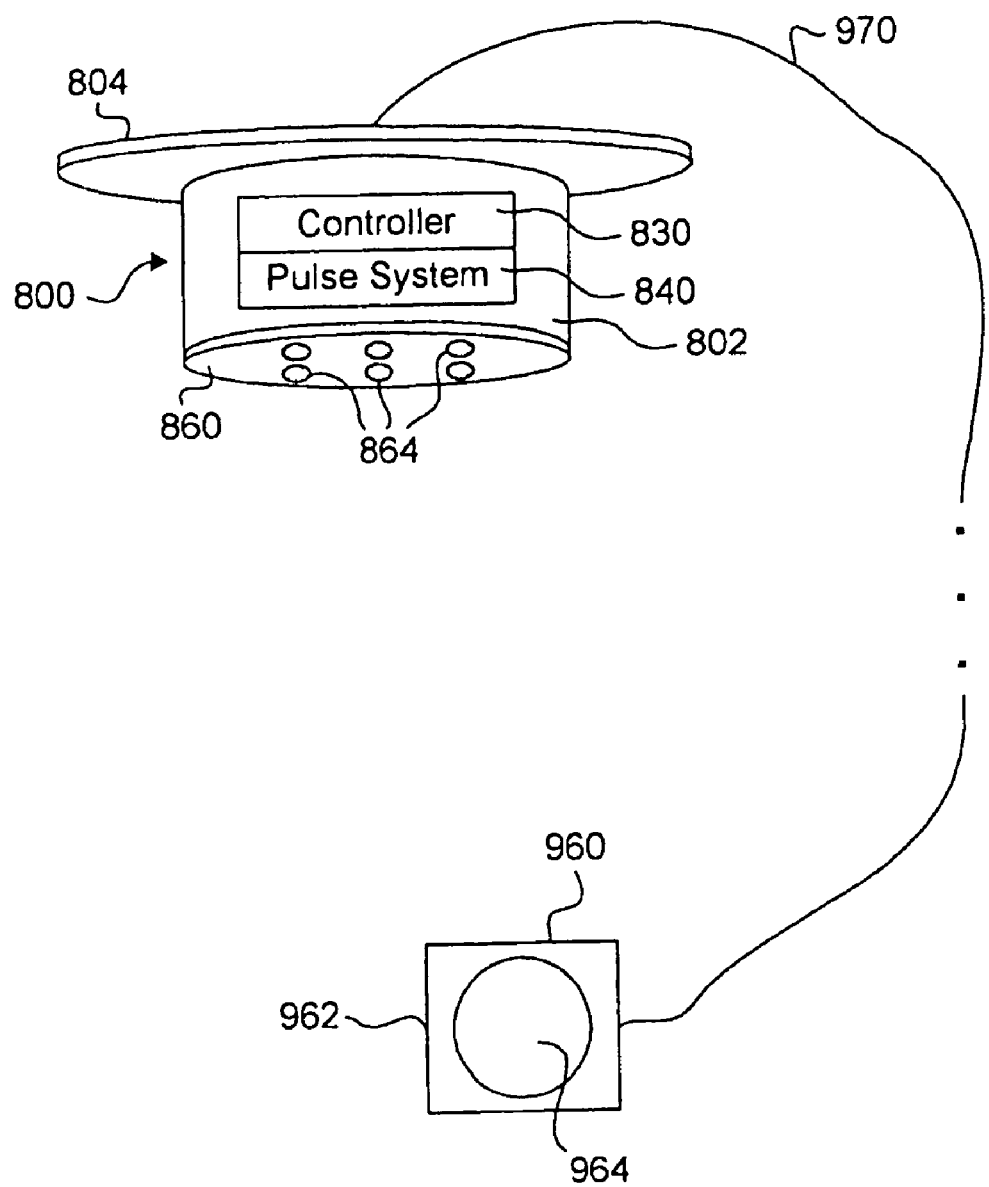
FIG. 9A is a schematic illustration of a system for applying electrical stimulation to a site on or proximate to the cortex in accordance with another embodiment of the invention.

FIG. 9A is a schematic illustration of a system for applying electrical stimulation to a surface site on or proximate to the cortex in accordance with another embodiment of the invention. Relative to FIGS. 8A, 8B, and 8C, like reference numbers indicate like elements. In one embodiment, the system comprises a support member 800 that carries a controller 830, a pulse system 840, and a local electrode assembly 860. The system may further include at least one remote electrode assembly 960. The support member 800 may include a housing 802 and an attachment element 804 as described above.

The local electrode assembly 860 may comprise a biasing element 862 that carries a first set of contacts 864. In one embodiment, the local electrode assembly 860 is coupled to the pulse system's first terminal 842a. The remote electrode assembly 960 may comprise a support member 962 that carries a second set of contacts 964, and may have a structure analogous to one or more types of electrodes described in U.S. patent application Ser. No. 10/877,830, which is incorporated herein by reference. Alternatively, the remote electrode assembly 960 may comprise a cranial screw or peg type electrode as described in U.S. patent application Ser. No. 10/418,796 (previously incorporated herein by reference); or a depth, deep brain, or other type of electrode. In certain embodiments, the remote electrode assembly 960 may provide an active or aggregate conductive surface area that is greater than an active or aggregate conductive surface area associated with the local electrode assembly 860 in a manner analogous to that described above. The remote electrode assembly 960 may be coupled to the pulse system's second terminal 842b by a link 970. Depending upon embodiment details, the pulse system's first and second terminals 842a–b may be configured as an anode and a cathode, possibly in a selective, programmable, deterministic, and/or pseudo-random manner.

The support member 800 may be implanted into or through a craniotomy that is above a stimulation site in a manner analogous to that described above. The remote electrode assembly 960 may be implanted or positioned distant or remote from the support member 800. The remote electrode assembly 960, for example, may be positioned upon or beneath the patient's skin at an anatomical location that is above or below the patient's neck; or within the patient's cranium at a cortical, subcortical, or deep brain location that is distant, distinct, or remote from the local electrode assembly 860. The local electrode assembly 860 may be biased in accordance with a first signal polarity, and the remote electrode assembly 960 may be biased in accordance with a second signal polarity to provide unipolar stimulation.

Figure 9B:
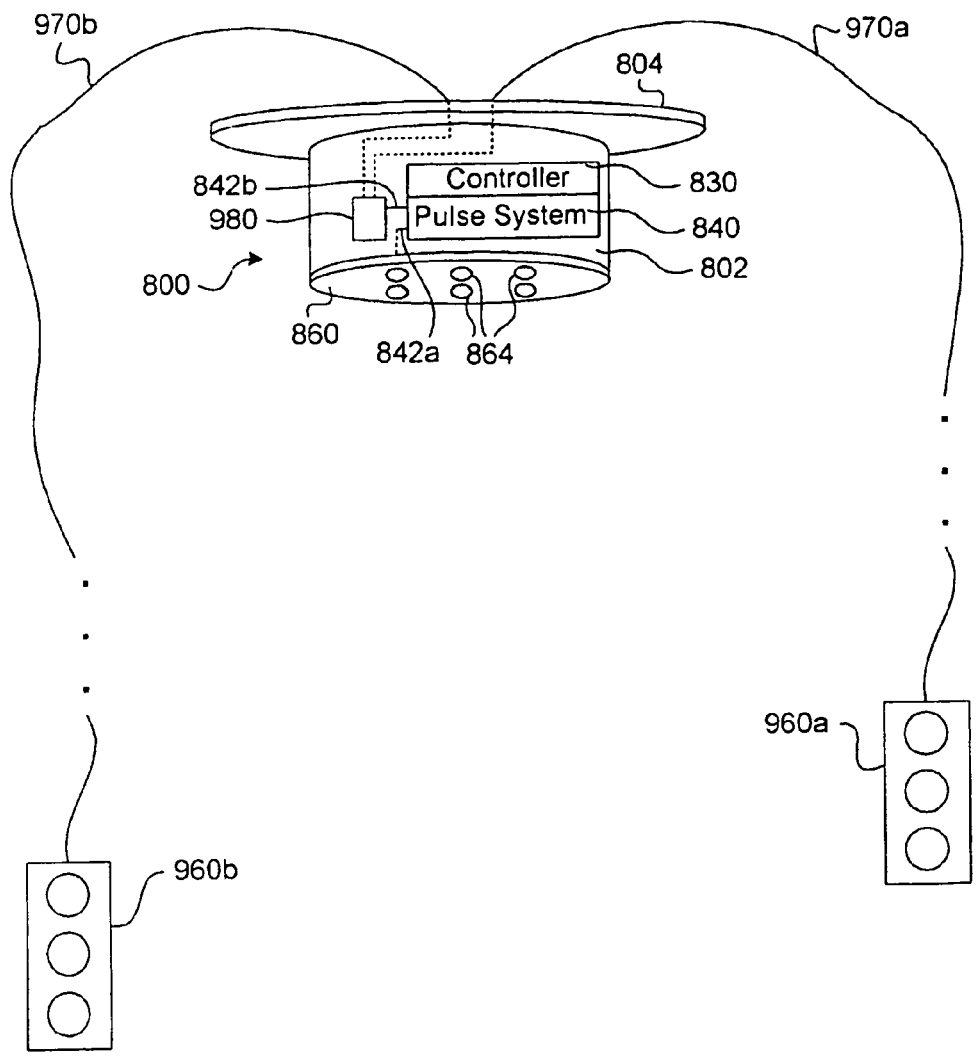
FIG. 9B is a schematic illustration of a system for applying electrical stimulation to a site on or proximate to the cortex in accordance with another embodiment of the invention.

FIG. 9B is a schematic illustration of a system for applying electrical stimulation to a surface site on or proximate to the cortex in accordance with another embodiment of the invention. Relative to FIG. 9A, like reference numbers indicate like elements. The embodiment shown in FIG. 9B includes a first and a second remote electrode assembly 960a–b, which may be identical, essentially identical, or different in structure. Any given remote electrode assembly 960a–b may comprise an electrode of a type indicated above. Depending upon embodiment details, the first and/or the second remote electrode assembly 960a–b may provide an active or aggregate conductive surface area that is greater than an active or aggregate conductive surface area associated with the local electrode assembly 860 in a manner analogous to that described above. The first and second remote electrode assemblies 960a–b are respectively coupled to the pulse system's second terminal 842b by a first and a second link 970a–b.

The embodiment shown in FIG. 9B may further include a signal selection module 980 that facilitates selectable or programmable coupling of the first and/or second remote electrode assembly 960a–b to the pulse system's second terminal 842b. Depending upon embodiment details and/or the nature of the patient's neurological condition, only one of the first and second remote electrode assemblies 960a–b may be coupled to the pulse system's second terminal 842b at any given time; or the first and second remote electrode assemblies 960a–b may be coupled to the second terminal 842b simultaneously.

In various embodiments, the support member 800 may be implanted at a stimulation site in a manner analogous to that described above. The first and second remote electrode assemblies 960a–b may be respectively positioned or implanted at a first and a second anatomical location that is distant, remote, or distinct from the stimulation site. The local electrode assembly 860 may be biased in accordance with a first signal polarity, while one or both of the remote electrode assemblies 960a–b may be biased in accordance with a second signal polarity at any given time to provide unipolar stimulation.

The use of multiple remote electrode assemblies 960a–b positioned at different anatomical locations may provide multiple current pathways through which neural stimulation may affect or influence particular target cortical and/or subcortical neural populations, neural structures, and/or neural projections, possibly in an alternating or time-dependent manner. For example, unipolar stimulation delivered or applied along or with respect to a first current pathway may be directed toward affecting neural activity in a first hemisphere of the brain, while unipolar stimulation applied with respect to a second current pathway may be directed toward affecting neural activity in a second hemisphere of the brain. Neural activity in each hemisphere may influence the development, recovery, and/or retention of functional abilities, possibly through neuroplastic mechanisms. In certain embodiments, one or more stimulation parameters such as stimulation signal frequency, amplitude, and/or polarity may differ or vary in accordance with a current pathway that is active or under consideration at any given time.

One or more embodiments described above may be modified to include or exclude elements or features described in association with other embodiments, for example a signal selection module 880, 980. Additionally or alternatively, particular embodiments may include multiple local electrode assemblies positioned at multiple stimulation sites, in conjunction with one or more remote electrode assemblies positioned distant from such stimulation sites to provide electrical continuity for unipolar stimulation.

B. Methods for Applying Electrical Stimulation

Figure 10:
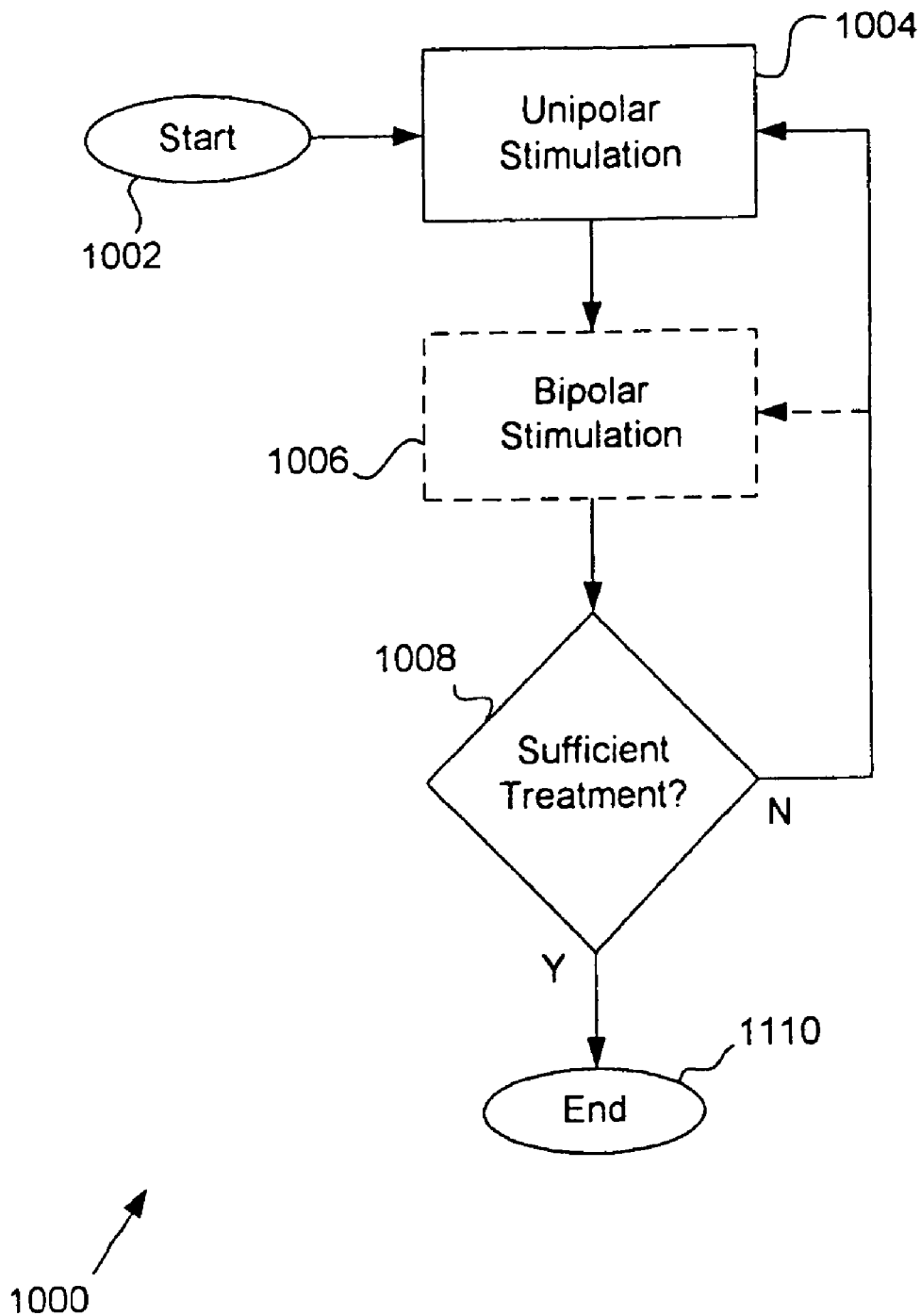
FIGS. 10–11 are flow charts illustrating methods for applying electrical stimulation to a stimulation site in accordance with embodiments of the invention.
Figure 11:
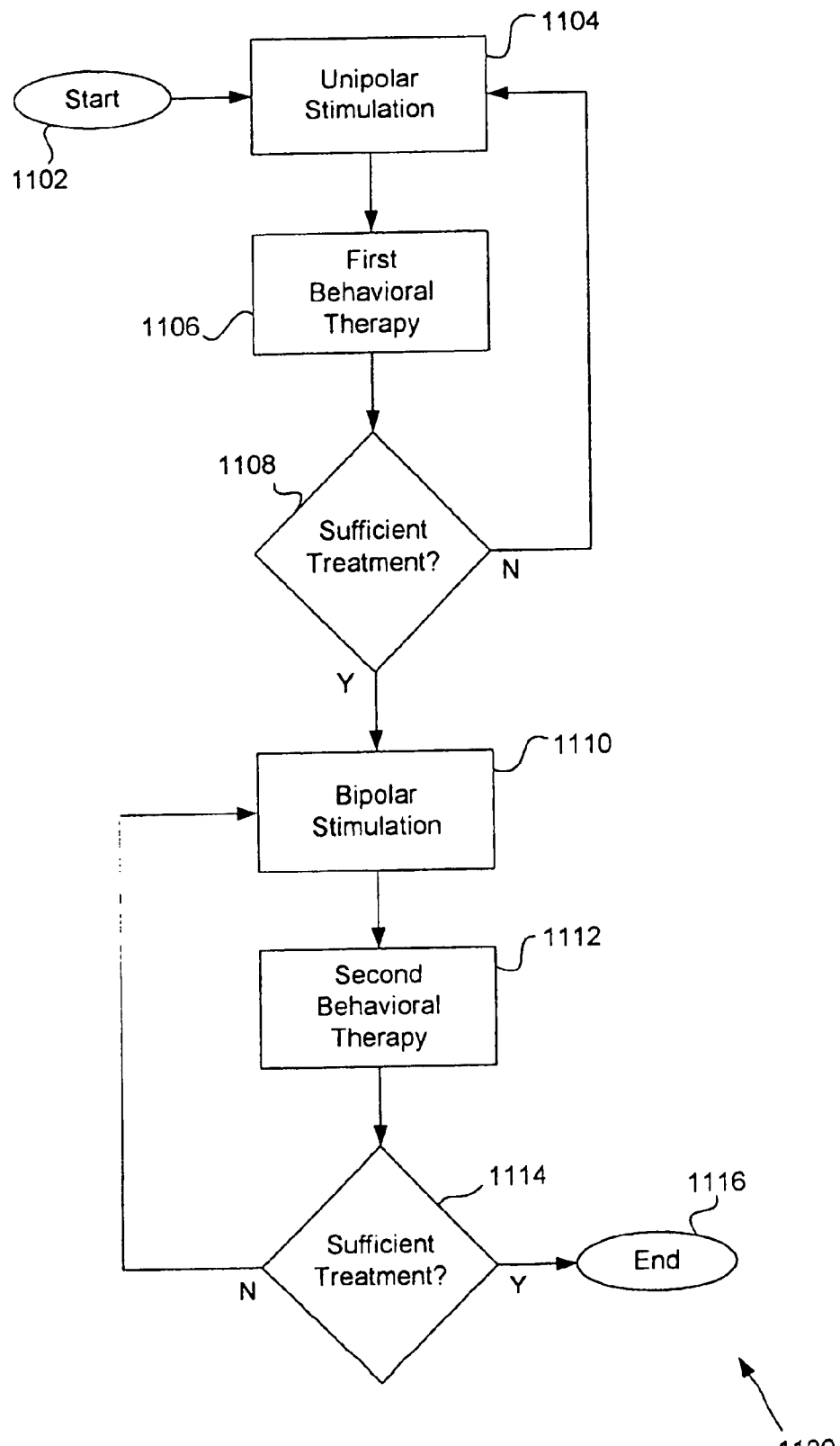

FIGS. 10–11 are flow charts illustrating various methods for applying neural stimulation to a stimulation site in accordance with the present invention. FIG. 10, more specifically, illustrates a method 1000 including a start procedure 1002, at least one unipolar stimulation procedure 1004, and a decision procedure 1008. The unipolar stimulation procedure 1004 includes establishing an electrical field by applying an electrical signal having an identical first signal polarity to a first set of contacts located at a stimulation site while applying a second signal polarity to a second set of contacts that is spaced apart or remote from the stimulation site. The unipolar stimulation procedure 1004 may involve the application of anodal unipolar stimulation and/or cathodal unipolar stimulation to the patient, possibly in a manner that increases or enhances a likelihood or rate of patient functional recovery and/or development. Moreover, the unipolar stimulation procedure 1004 may involve the application or delivery of stimulation signals at a subthreshold and/or a suprathreshold level relative to the generation of a statistically and/or functionally significant number of action potentials in one or more target neural populations. The unipolar stimulation procedure 1004 may also involve the application or theta burst stimulation signals during one or more time periods.

The unipolar stimulation procedure 1004 can be performed using any of the systems set forth above with respect to FIGS. 1–9B. The second set of contacts can be located apart from the stimulation site along a vector that passes through deep layers of the cortex and/or other neural regions in a direction that is oblique, and generally approximately normal, with respect to the first set of contacts at the stimulation site. The unipolar stimulation procedure 1004, for example, may involve applying a cathodal and/or an anodal signal to a set of active surface contacts 164a to restore or at least partially recover speech, movement, and/or other functions that have been impaired by stroke or other brain damage.

An optional or alternative embodiment of the method 1000 can further include at least one bipolar stimulation procedure 1006 in which a first set of contacts at a stimulation site are biased at a first signal polarity, while a second set of contacts at a stimulation site are biased at a second signal polarity. The bipolar stimulation procedure 1006 may be performed in a manner identical or analogous to that described above, and may involve the delivery of stimulation signals at a subthreshold and/or a suprathreshold level. The bipolar stimulation procedure 1006 may also involve the application of theta burst stimulation signals during one or more time periods.

The decision procedure 1008 may decide whether the stimulation has been of sufficient or adequate duration and/or effect. In particular embodiments, the decision procedure 1008 may involve monitoring or measuring patient progress and/or functional capabilities through one or more standardized measures, tests, or tasks. Such standardized measures may include or be based upon, for example, a Fugl-Meyer Assessment of Sensorimotor Impairment; a National Institute of Health (NIH) Stroke Scale; a Stroke Impact Scale (SIS); an ADL scale; a Quality of Life (QoL) scale; physical measures such as grip strength or finger tapping speed; a neuropsychological testing battery; a walking, movement, and/or dexterity test; a behavioral test; a language test; a comprehension test; and/or other measures of patient functional ability. In certain embodiments, the decision procedure 1008 may alternatively or additionally involve an electrophysiological signal acquisition and/or analysis procedure, and/or a neural imaging procedure (e.g., MRI, fMRI, or PET). The decision procedure 1008 may direct the method 1000 to apply either a unipolar stimulation procedure 1004 and/or a bipolar stimulation procedure 1006 depending upon the particular characteristics of the therapy and/or the nature or extent of the patient's neurofunctional condition. One or more stimulation sites and/or stimulation parameters (e.g., pulse repetition frequency, first phase pulse width, peak current and/or voltage amplitude, theta burst characteristics, a waveform variation and/or modulation function, and/or other parameters) corresponding to particular unipolar and/or bipolar stimulation procedures 1004, 1006 may be identical, generally identical, or different depending upon the nature of a patient's neurologic dysfunction, patient condition, and/or embodiment details. The method 1000 may further include a termination procedure 1010 that is performed based upon the outcome of the decision procedure 1008.

FIG. 11 illustrates a method 1100 in accordance with another embodiment of the invention. In one embodiment, the method 1100 includes a start procedure 1102, a unipolar stimulation procedure 1104, and possibly a first adjunctive or synergistic therapy procedure 1106. The unipolar stimulation procedure 1104 may involve the application or delivery of anodal and/or cathodal unipolar stimulation signals to the patient, possibly in a manner that increases or enhances a likelihood and/or rate of patient functional recovery and/or development. Moreover, the unipolar stimulation procedure 1104 may involve subthreshold and/or suprathreshold stimulation, and/or theta burst stimulation during one or more time periods.

The unipolar stimulation procedure 1104 and the first adjunctive therapy procedure 1106 can be performed concurrently or serially depending upon the nature and/or extent of a patient's neurologic dysfunction, patient condition, and/or embodiment details. The first adjunctive therapy procedure 1106 may comprise a behavioral therapy procedure that can include a physical therapy, an activity of daily living, an intentional use of an affected body part, a speech therapy, a vision therapy, an auditory task or therapy (e.g., an auditory discrimination task), a reading task, a memory task, a visualization, imagination, or thought task, and/or another type of task or therapy. A subthreshold unipolar stimulation procedure 1104 may be performed concurrent with a first behavioral therapy procedure 1106 to enhance or maximize a likelihood generating action potentials that may subserve the development and/or recovery of one or more functional abilities.

The method 1100 may additionally include a first decision procedure 1108 that may decide whether the unipolar stimulation procedure 1104 and/or the first adjunctive therapy procedure 1106 have been of sufficient or adequate duration and/or effect. The first decision procedure 1108 may involve measurement or assessment of patient status, progress, and/or functional capabilities using one or more standardized measures, tests, or tasks; an electrophysiological signal acquisition and/or analysis procedure; and/or a neural imaging procedure. If additional unipolar stimulation and/or adjunctive therapy is warranted, the method 1100 may continue, resume, or restart a unipolar stimulation procedure 1104 and/or a first adjunctive therapy procedure 1106.

In certain embodiments, the method 1100 may further include a bipolar stimulation procedure 1110, and/or a second adjunctive or synergistic therapy procedure 1112. The bipolar stimulation procedure 1110 may involve the application or delivery of stimulation signals at a subthreshold and/or suprathreshold level, and may possibly involve theta burst stimulation at one or more times. The bipolar stimulation procedure 1110 may be directed toward the same, essentially the same, or different target neural structures, target neural projections, and/or target neural populations than the unipolar stimulation procedure 1104. Thus, the bipolar stimulation procedure 1110 may deliver or apply stimulation signals to the same or a different stimulation site than the unipolar stimulation procedure 1104, either in the same and/or a different brain hemisphere. For example, both the unipolar and bipolar stimulation procedures 1104, 1110 may deliver stimulation signals to identical or essentially identical portions of a patient's motor cortex; or the unipolar stimulation procedure 1104 may apply stimulation signals to portions of the patient's motor cortex, while the bipolar stimulation procedure 1110 may apply stimulation signals to portions of the patient's premotor cortex or another region of the brain.

The second adjunctive therapy procedure 1112 may involve, for example, a drug therapy and/or a behavioral therapy that is identical or essentially identical to or different from a therapy associated with the first adjunctive therapy procedure 1106. The second adjunctive therapy procedure 1112 may involve, for example, a visualization procedure such as thinking about performing one or more types of motions and/or tasks, while the first adjunctive therapy procedure 1106 may involve attempting to actually perform such motions and/or tasks.

Depending upon the nature and/or extent of a patient's neurologic dysfunction, patient condition, and/or embodiment details, the bipolar stimulation procedure 1110 and the second adjunctive therapy procedure 1112 may be performed concurrently or serially, in a manner analogous to that described above for the unipolar stimulation procedure 1104 and the first adjunctive therapy procedure 1106. Moreover, the bipolar stimulation procedure 1110 and/or the second adjunctive therapy procedure 1112 may precede or follow the unipolar stimulation procedure 1104 and/or the first adjunctive therapy procedure 1106 in either a generally continuous or an interrupted manner.

The method 1100 may further include a second decision procedure 1114 that may decide whether the bipolar stimulation procedure 1110 and/or the second adjunctive therapy procedure 1112 have been of sufficient or adequate duration and/or effect. The second decision procedure 1114 may involve measurement or assessment of patient status, progress, and/or functional capabilities using one or more standardized measures, tests, or tasks; an electrophysiological signal acquisition and/or analysis procedure; and/or a neural imaging procedure. If additional bipolar stimulation and/or adjunctive therapy is warranted, the method 1100 may continue, resume, or restart a bipolar stimulation procedure 1110 and/or a second adjunctive therapy procedure 1112. Finally, the method 1100 may include a termination procedure 1116 that may be performed based upon an outcome of the first and/or second decision procedure 1108, 1116.

Depending upon embodiment details, a method 1100 may comprise a number of anodal unipolar, cathodal unipolar, and/or bipolar stimulation procedures 1104, 1110, where the number, duration of, and/or time between such procedures and/or the particular stimulation sites to which such procedures are directed may be identical, essentially identical, or different. Moreover, one or more stimulation signal parameters (e.g., pulse repetition frequency, first phase pulse width, peak current and/or voltage amplitude, theta burst characteristics, a waveform variation and/or modulation function, and/or other parameters) corresponding to particular unipolar and/or bipolar stimulation procedures 1104, 1110 may be identical, generally identical, or different depending upon the nature of a patient's neurologic dysfunction, patient condition, and/or embodiment details.

In certain embodiments, one or more procedures described herein may form portions of a limited duration treatment program, in a manner analogous to that described in U.S. application Ser. No. 10/606,202, incorporated herein by reference. In accordance with various embodiments of the present invention, a limited duration treatment program may apply or deliver unipolar stimulation, and possibly bipolar stimulation, to a patient for a limited period of time to facilitate or effectuate complete, essentially complete, significant, or partial rehabilitation, restoration, or functional healing of or recovery from a neurological condition such as a neurological malfunction and/or a neurologically based deficit or disorder. Depending upon the extent or nature of the patient's neurological condition and/or functional deficits, a limited duration treatment program may last, for example, a number of weeks, months, or possibly one or more years.

From the foregoing, it will be appreciated that specific embodiments of the invention have been described herein for purposes of illustration, but that various modifications may be made without deviating from the spirit and scope of the invention. For example, aspects of the invention described in the context of particular embodiments can be combined or eliminated in other embodiments. Accordingly, the invention is not limited except as by the appended claims.

We claim:

1. A system for applying electrical stimulation to a patient's brain, comprising:
    an implantable housing;
    a pulse generator carried by the implantable housing, the pulse generator having a first terminal and a second terminal, the pulse generator being configured to deliver to at least one of the first and second terminals a stimulation signal having a plurality of stimulation periods with at least one of the stimulation periods having a duration of about 30 seconds or less;
    at least one first electrode carried by the housing and operatively coupled to at least one of the first and second terminals; and
    at least one second electrode carried by the housing and operatively coupled to at least one of the first and second terminals, wherein the housing includes a first portion and a second portion, and wherein the at least one first electrode is carried by the first portion of the housing so as to be positioned at a cortical stimulation site of the patient located at least approximately at or below an inner surface of the patient's skull when the housing is implanted, and wherein the at least one second electrode is carried by the second portion of the housing so as to be positioned at least approximately at or above an outer surface of the patient's skull and beneath the patient's scalp when the housing is implanted.

2. The system of claim 1 wherein the pulse generator is configured to deliver the stimulation signal with at least one of the stimulation periods having a duration of about 10 seconds or less.

3. The system of claim 1 wherein the pulse generator is configured to deliver the stimulation signal with at least one of the stimulation periods having a duration of about one second or less.

4. The system of claim 1 wherein the pulse generator is configured to deliver the stimulation signal with at least one of the stimulation periods having a duration of less than one second.

* * * * *